US012569421B2

(12) United States Patent
Goutsis et al.

(10) Patent No.: US 12,569,421 B2
(45) Date of Patent: Mar. 10, 2026

(54) AGENTS FOR OXIDATIVELY CHANGING THE COLOR OF KERATIN FIBERS, COMPRISING A COMPLEXING AGENT, AN ACTIVATOR, AND AN OXIDANT

(71) Applicant: Henkel AG & Co. KGaA, Duesseldorf (DE)

(72) Inventors: Konstantin Goutsis, Juechen (DE); Daniela Kessler-Becker, Leverkusen (DE)

(73) Assignee: Henkel AG & Co. KGaA, Düsseldorf (DE)

( * ) Notice: Subject to any disclaimer, the term of this patent is extended or adjusted under 35 U.S.C. 154(b) by 320 days.

(21) Appl. No.: 18/270,231

(22) PCT Filed: Dec. 6, 2021

(86) PCT No.: PCT/EP2021/084395
§ 371 (c)(1),
(2) Date: Jun. 29, 2023

(87) PCT Pub. No.: WO2022/148581
PCT Pub. Date: Jul. 14, 2022

(65) Prior Publication Data

US 2024/0115474 A1 Apr. 11, 2024

(30) Foreign Application Priority Data

Jan. 5, 2021 (DE) ..................... 10 2021 200 031.2

(51) Int. Cl.

| | |
|---|---|
| ***A61Q 5/10*** | (2006.01) |
| ***A61K 8/22*** | (2006.01) |
| ***A61K 8/44*** | (2006.01) |
| ***A61K 8/46*** | (2006.01) |
| ***A61K 8/55*** | (2006.01) |
| ***A61K 8/64*** | (2006.01) |
| ***A61Q 5/08*** | (2006.01) |

(52) U.S. Cl.
CPC .................. *A61K 8/44* (2013.01); *A61K 8/22* (2013.01); *A61K 8/46* (2013.01); *A61K 8/553* (2013.01); *A61K 8/64* (2013.01); *A61Q 5/08* (2013.01); *A61K 2800/522* (2013.01); *A61K 2800/882* (2013.01)

(58) Field of Classification Search
CPC ... A61K 8/44; A61K 8/22; A61K 8/46; A61K 8/553; A61K 8/64; A61K 2800/522; A61K 2800/882; A61K 2800/30; A61K 8/355; A61K 8/361; A61K 8/645; A61K 8/65; A61K 8/67; A61Q 5/08; A61Q 5/10
USPC .............................................................. 8/405
See application file for complete search history.

(56) References Cited

U.S. PATENT DOCUMENTS

| | | | | |
|---|---|---|---|---|
| 2005/0011017 | A1 | 1/2005 | Legrand et al. | |
| 2019/0224095 | A1 | 7/2019 | Scheunemann et al. | |
| 2022/0031592 | A1* | 2/2022 | Hodes ...................... | A61Q 5/10 |

FOREIGN PATENT DOCUMENTS

| | | | | |
|---|---|---|---|---|
| DE | 102008034845 A1 | | 2/2010 | |
| DE | 102008046883 A1 | * | 3/2010 | ............... A61Q 5/00 |
| DE | 102016218989 A1 | | 4/2018 | |
| DE | 102018123507 A1 | * | 3/2020 | ............... A61Q 5/10 |
| EP | 1462090 A1 | | 9/2004 | |
| EP | 1714634 A1 | | 10/2006 | |
| EP | 1602356 B1 | | 3/2009 | |
| EP | 3290020 A1 | | 3/2018 | |
| WO | 2022058147 A2 | | 3/2022 | |

OTHER PUBLICATIONS

STIC Search Report dated Jul. 9, 2025.*
Database Gnpd "Very Long Lasting Permanent Hair Colorant" Dec. 30, 2020.*
Database Gnpd "Permanent Colorant Gel" dated Jul. 29, 2020.*
Search report dated Apr. 26, 2022, from parallel PCT application No. PCT/EP2021/084395, 18 pages, for information purpose only.
Database GNPD [Online] MINTEL, "Very Long Lasting Permanent Hair Colourant", anonymous, Dec. 30, 2020.
Database GNPD [Online] MINTEL, "Permanent Colouring Gel", anonymous, Jul. 29, 2020.
Database GNPD [Online] MINTEL, "Repigment Care Synergic Treatments 2in1", anonymous, Sep. 2, 2016.
Database GNPD [Online] MINTEL, "Permanent Hair Colour", anonymous, Sep. 3, 2020.

* cited by examiner

*Primary Examiner* — Eisa B Elhilo
(74) *Attorney, Agent, or Firm* — Blank Rome LLP

(57) ABSTRACT

An agent for oxidatively changing the color of keratin fibers, such as human hair, may include at least one complexing agent of the general formula (I); at least one activator from the group of amino acids, protein hydrolyzates, and radical scavengers; and at least one oxidant.

(I)

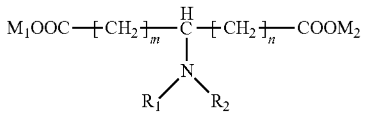

15 Claims, No Drawings

AGENTS FOR OXIDATIVELY CHANGING THE COLOR OF KERATIN FIBERS, COMPRISING A COMPLEXING AGENT, AN ACTIVATOR, AND AN OXIDANT

CROSS-REFERENCE TO RELATED APPLICATION

The present application is a national stage entry according to 35 U.S.C. § 371 of PCT application No.: PCT/EP2021/084395 filed on Dec. 6, 2021; which claims priority to German patent application 10 2021 200 031.2 filed on Jan. 5, 2021; all of which are incorporated herein by reference in their entirety and for all purposes.

TECHNICAL FIELD

The present invention is in the field of cosmetics and relates to agents for oxidatively changing the color of keratin fibers, and in particular human hair. These agents are characterized in that they contain at least one complexing agent (a) of formula (I), at least one activator (b) of the group of amino acids, protein hydrolyzates, and radical scavengers, and furthermore at least one oxidant (c).

A second subject matter relates to a method for oxidatively changing the color of keratin fibers—in particular, human hair—wherein an agent of the first subject matter is applied to the keratin fibers and rinsed out again after a contact time.

BACKGROUND

Changing the form and color of hair represents an important area in modern cosmetics. In addition to coloring, the lightening of the natural hair color, or hair bleaching, is a very specific desire of many consumers, since a blond hair color is regarded as attractive and desirable in terms of fashion. Various bleaching agents with different bleaching power are commercially available for this purpose.

The oxidizing agents contained in hair-bleaching agents are capable of lightening hair fibers by oxidative destruction of the hair's own melanin dye. For a moderate hair-bleaching effect it is sufficient to use hydrogen peroxide—optionally with the use of ammonia or other alkalizing agents—as the only oxidizing agent; to achieve a stronger hair-bleaching effect, it is usual to use a mixture of hydrogen peroxide and peroxodisulfate salts and/or peroxomonosulfate salts.

In the case of dark starting hair, longer application times and/or repeated bleaching processes are usually necessary in order to lighten the hair over several shades. However, this is also accompanied by greater damage to the hair, since not only the colors of the hair, but also the rest of the structural components of the hair are oxidatively damaged. Depending upon the extent of the damage, it ranges from coarse, brittle, and tangled hair, over a reduced resistance and tear resistance of the hair, to hair breakage.

The use of complexing agents in oxidative color changes of keratin fibers is known in the prior art. The complexing agents are, among other things, to prevent breakdown of the hydrogen peroxide by metal ions accumulated in the hair fibers.

For example, EP 1714634 A1 describes a hair-treatment kit for coloring human hair, comprising a first compartment, which contains a complexing agent, and a second compartment, which contains coloring agents. Undesirable reactions on and with hair that lead to an undesirable heating are to be prevented by the use of a complexing agent.

In many bleaching products on the market, the complexing agents used are HEDP (etidronic acid) or salts thereof, or EDTA (ethylenediamine tetraacetic acid or ethylenediamine tetraacetate) or salts thereof. Both HEDP and EDTA stabilize hydrogen peroxide in an effective manner and complex metal ions present efficiently enough that an undesired temperature increase taking place during application is virtually completely avoided. However, the major disadvantage of HEDP and EDTA is their poor biodegradability. In recent times, the user increasingly considers the ecological profile of the cosmetic products used by them. For example, the user prefers, in particular, cosmetics that are as sustainable as possible, containing biodegradable ingredients.

The use of substances of natural origin as complexing agents is also already known in the literature. For example, EP 1462090 A1 describes agents for bleaching, coloring, or shaping hair, which contain the combination of at least one oxidant and at least one polyhydroxycarboxylic acid.

Furthermore, EP 1602356 B1 describes decolorizing agents or bleaching agents in which the biodegradable complexing agent ethylene diamine-N,N'-disuccinic acid in combination with a persulfate is used.

However, the performance properties of the agents described in the aforementioned documents are still in need of improvement, and in particular the bleaching power cannot yet be considered to be optimal. The temperature development occurring on the head during the application also requires further improvement.

It was an objective to find hair treatment agents, and in particular bleaching agents or agents for oxidative color change, containing biodegradable complexing agents, which are as superior as possible to the bleaching or lightening agents known from the prior art with regard to their bleaching performance. Furthermore, the bleaching agents should have a sufficiently high stability and, even when used on hair with a higher metal or heavy metal content, should not heat up too much. In addition, when the complexing agents are used in lightening or bleaching agents, the hair damage should be reduced, and the handling or the hair feel should be improved as much as possible.

SUMMARY

Surprisingly, it has now been found that this objective can be achieved in its entirety when an agent is used on the keratin fibers which, in addition to the oxidant (c) responsible for the lightening, furthermore contains at least one specific complexing agent (a) of formula (I) and an activator from a specific group (b).

A first subject matter is an agent for oxidatively changing the color of keratin fibers, and in particular human hair, containing (a) at least one complexing agent of general formula (I),

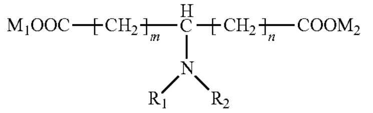

(I)

where

R1, R2, independently of one another, represent a carboxy-$C_1$-$C_6$ alkyl group or a physiologically acceptable salt thereof, a hydrogen atom, a $C_1$-$C_6$ alkyl group, or a hydroxy-$C_2$-$C_6$ alkyl group, and m represents an integer from 0 to 6, and n represents an integer from 0 to 6, and M1, M2, independently of one another, represent a hydrogen atom or an equivalent of an alkali metal ion, alkaline earth metal ion, or metal ion—preferably sodium, potassium, ½ magnesium, ½ calcium, ½ zinc—or an ammonium ion ($NH_4^+$), and (b) at least one activator from the group of amino acids, protein hydrolyzates, and radical scavengers, and (c) at least one oxidant.

DETAILED DESCRIPTION

Keratin Fibers

"Keratinic fibers" or also "keratin fibers" are to be understood in this context as furs, wool, feathers, and in particular human hair. Although the agents are primarily suitable for treating or lightening keratin fibers, and in particular human hair, nothing in principle conflicts with use in other fields as well.

Agent for Oxidatively Changing the Color of Keratin Fibers

The expression, "oxidatively changing the color," used in principle comprises any possible form of treatment in which the coloring of the keratin fibers is changed using at least one oxidant. In particular, the agents for oxidative coloring may be used for providing a lightened color, for providing a lighter shade, and for lightening, wherein the lightening can alternatively also be referred to as bleaching or as decolorizing. A lightening is understood to mean any form of color change of the fibers in which the keratin fibers have a lighter coloring compared to the color present before the application of the agent. The lightened coloring of the hair is brought about by at least one oxidant present in the agent. In addition to the one or more oxidants, the agents can also for lightening purposes contain coloring components, such as oxidation dye precursors and/or direct dyes. The color effect of the resulting coloring can, during lightening, be easily modified by the coloring components. However, these coloring components are preferably contained in the agent in such small amounts that the color impression of the keratin fibers treated with the agent nevertheless is lighter than their original color. Corresponding coloring techniques can also be referred to as coloring bleaching or as nuanced bleaching.

The agent contains the components (a), (b), and (c) in an optional cosmetic carrier. For example, a suitable aqueous, alcoholic, or aqueous-alcoholic carrier can be used as cosmetic carrier for the agent. For the purpose of hair coloring, such carriers are for example creams, emulsions, gels, pastes, or also surfactant-containing foaming solutions, such as shampoos, foam aerosols, foam formulations, or other preparations which are suitable for application to hair.

The agent is consequently preferably an agent for oxidatively changing the color of keratin fibers, and in particular human hair, containing in a cosmetic carrier (a) at least one complexing agent of general formula (I), (I)

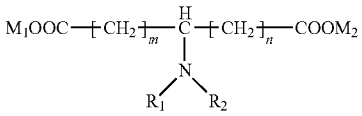

where

R1, R2, independently of one another, represent a carboxy-$C_1$-$C_6$ alkyl group or a physiologically acceptable salt thereof, a hydrogen atom, a $C_1$-$C_6$ alkyl group, or a hydroxy-$C_2$-$C_6$ alkyl group, and m represents an integer from 0 to 6, and n represents an integer from 0 to 6, and M1, M2, independently of one another, represent a hydrogen atom or an equivalent of an alkali metal ion, alkaline earth metal ion, or metal ion—preferably sodium, potassium, ½ magnesium, ½ calcium, ½ zinc—or an ammonium ion ($NH_4^+$), and (b) at least one activator from the group of amino acids, protein hydrolyzates, and radical scavengers, and (c) at least one oxidant.

This agent is a ready-to-use agent which can be applied to the keratin fibers in this form for the purpose of bleaching or lightening or oxidative dyeing.

Complexing Agent (a)

As the first ingredient, the agent contains at least one complexing agent (a) of general formula (I), (I)

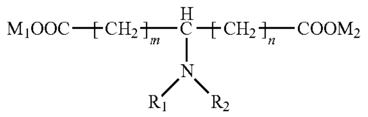

where

R1, R2, independently of one another, represent a carboxy-$C_1$-$C_6$ alkyl group or a physiologically acceptable salt thereof, a hydrogen atom, a $C_1$-$C_6$ alkyl group, or a hydroxy-$C_2$-$C_6$ alkyl group, and m represents an integer from 0 to 6, and n represents an integer from 0 to 6, and M1, M2, independently of one another, represent a hydrogen atom or an equivalent of an alkali metal ion, alkaline earth metal ion, or metal ion—preferably sodium, potassium, ½ magnesium, ½ calcium, ½ zinc—or an ammonium ion ($NH_4^+$).

The complexing agents of formula (I) are described as biodegradable and therefore represent an ecologically advantageous replacement for HEDP and EDTA. Surprisingly, it has been found in addition that the bleaching power could also be massively improved using these special complexing agents (a) in the agent.

Examples of the substituents R1 to R5 stated in formula (I) are listed below by way of example:

Examples of $C_1$-$C_6$ alkyl groups are $—CH_3$, $—CH_2CH_3$, $—CH_2CH_2CH_3$, $—CH(CH_3)_2$, $—CH_2CH(CH_3)_2$, $—CH(CH_3)CH_2CH_3$, $—C(CH_3)_3$, $—(CH_2)_4CH_3$, $—(CH_2)_5CH_3$. Methyl and ethyl are particularly preferred alkyl groups. Examples of $C_1$-$C_6$ hydroxyalkyl groups are $—CH_2OH$, $—CH_2CH_2OH$, $—CH_2CH_2CH_2OH$, $—CH_2CH(OH)CH_3$, $—CH_2CH_2CH_2CH_2OH$, where $—CH_2CH_2OH$ is preferred.

Examples of carboxy-$C_1$-$C_6$ alkyl groups are $HOOC—CH_2—$, $HOOC—CH_2—CH_2—$, $HOOC—CH_2—CH_2—CH_2—$, $HOOC—CH_2—CH_2—CH_2—CH_2—$, where the group $HOOC—CH_2—$ is preferred.

In the complexing agents of the general formula (I), the groups R1 and R2 independently of one another represent a carboxy-$C_1$-$C_6$ alkyl group or a physiologically acceptable salt thereof, a hydrogen atom, a $C_1$-$C_6$ alkyl group, or a hydroxy-$C_2$-$C_6$ alkyl group.

Physiologically acceptable salts are understood to mean the salts which can be used in cosmetics under physiological conditions without disadvantageous effect. Examples of a physiologically acceptable salt of a carboxyl group are the sodium salt, the potassium salt, and the ammonium salt. Examples of a physiologically acceptable salt of a carboxy-$C_1$-$C_6$ alkyl group are, for example, the sodium salt, the potassium salt, and the ammonium salt of the carboxy-$C_1$-$C_6$ alkyl group.

A particularly strong improvement in the bleaching power was observed when using agents which contained at least one complexing agent (a) of general formula (I), where the groups R1 and R2 independently of one another represent a carboxy-$C_1$-$C_6$ alkyl group or a physiologically acceptable salt thereof.

In the context of a further particularly preferred embodiment, an agent is characterized in that it contains at least one complexing agent (a) of general formula (I), where R1, R2, independently of one another, represent a carboxy-$C_1$-$C_6$ alkyl group or a physiologically acceptable salt thereof.

Very particularly preferably, R1 and R2, independently of one another, represent a carboxy-$C_1$-$C_6$ alkyl group or a physiologically acceptable salt thereof. Explicitly, very particularly preferably, R1 and R2, independently of one another, represent a carboxymethyl group or a physiologically acceptable salt thereof.

In the context of an explicitly very particularly preferred embodiment, an agent is characterized in that it contains at least one complexing agent (a) of general formula (I), where R1, R2, independently of one another, represent a carboxymethyl group or a physiologically acceptable salt thereof.

In the context of an explicitly very particularly preferred embodiment, an agent is characterized in that it contains at least one complexing agent (a) of general formula (I), where R1, R2 both represent a carboxymethyl group or a physiologically acceptable salt thereof.

In the complexing agents of general formula (I), the index number m represents an integer from 0 to 6. The index number m indicates the number of methylene groups (i.e., —$CH_2$ groups) which are between the structural unit —$COOM_1$ and the carbon atom bearing the grouping —$NR_1R_2$. Particularly good results were obtained when complexing agents of formula (I) were used in which m represented the number 0 or 1, and very particularly preferably the number 0.

In the complexing agents of general formula (I), the index number n represents an integer from 0 to 6. The index number n indicates the number of methylene groups (i.e., —$CH_2$ groups) which are located between the carbon atom bearing the grouping —NR1R2 and the grouping —$COOM_2$. In this context, particularly good results were obtained when complexing agents of formula (I) were used in which n represented the number 0, 1, or 2, and very particularly preferably the number 2.

In the context of a further particularly preferred embodiment, an agent is characterized in that it contains at least one complexing agent (a) of general formula (I), where m represents the number 0 or 1, and preferably the number 0, and/or n represents the number 0, 1, or 2, and preferably the number 2.

In the context of a further particularly preferred embodiment, an agent is characterized in that it contains at least one complexing agent (a) of general formula (I), where m represents the number 0, and n represents the number 2.

If R1 and R2, independently of one another, represent a carboxymethyl group or a physiologically acceptable salt thereof, m represents the number 0, and n represents the number 2, then the complexing agent (a) has the general structural formula (Ia).

In the context of a particularly preferred embodiment, an agent is characterized in that it contains at least one complexing agent (a) of general formula (Ia), (Ia)

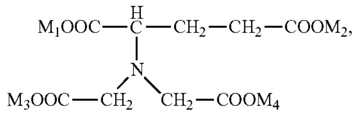

where

M1, M2, independently of one another, represent a hydrogen atom or an equivalent of an alkali metal ion, alkaline earth metal ion, or metal ion—preferably sodium, potassium, ½ magnesium, ½ calcium, ½ zinc—or an ammonium ion ($NH_4^+$), and M3, M4, independently of one another, represent a hydrogen atom or an equivalent of an alkali metal ion, alkaline earth metal ion, or metal ion—preferably sodium, potassium, ½ magnesium, ½ calcium, ½ zinc—or an ammonium ion ($NH_4^+$).

To achieve the object, it has been found to be very particularly advantageous if M1, M2, M3, and M4, independently of one another, represent a sodium cation ($Na^+$) or a potassium cation ($K^+$).

In the context of a particularly preferred embodiment, an agent is characterized in that it contains at least one complexing agent (a) of general formula (Ia), (Ia)

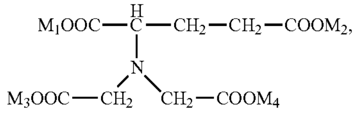

where

M1, M2, independently of one another, represent sodium or potassium, and

M3, M4, independently of one another, represent sodium or potassium.

An explicitly very particularly preferred complexing agent (a) of this embodiment is tetrasodium N,N-bis(carboxylatomethyl)-L-glutamate. Tetrasodium N,N-bis(carboxylatomethyl)-L-glutamate falls under the formula (Ia), where M1, M2, M3, and M4 represent a sodium cation.

Tetrasodium N,N-bis(carboxylatomethyl)-L-glutamate can alternatively also be referred to as glutamic acid N,N diacetic acid tetrasodium salt. The L-form carries the name L-tetrasodium N,N-bis(carboxylatomethyl)-L-glutamate or (S)-glutamic acid N,N diacetic acid tetrasodium salt, N,N-bis(carboxymethyl)-L-glutamic acid tetrasodium salt, or GLDA-$Na_4$ for short and has the CAS number 51981-21-6. The INCI name of this compound is TETRASODIUM GLUTAMATE DIACETATE.

Under the trade name, Aquacid 2015 EX, tetrasodium N,N-bis(carboxymethyl)-L-glutamates can be purchased commercially—for example, from Aquaphararm Chemicals.

From Akzo Nobel, N,N-bis(carboxymethyl) glutamic acid tetrasodium salt is commercially sold under the trade name, Dissolvine GL PD S (CAS number 51981-21-6).

GLDA has a stereogenic center. Both the (S)-form and the (R)-form (or both the L-form and the D-form) may be used.

For further optimization of the bleaching or lightening effect, the one or more complexing agents (a) are preferably used in certain quantity ranges in the agent. The agent very particularly preferably contains—in relation to the total weight of the agent—one or more complexing agents (a) of formula (I) in a total amount of 0.01 to 10.0 wt %, preferably of 0.05 to 7.5 wt %, more preferably of 0.1 to 5.0 wt %, and very particularly preferably of 0.3 to 3.5 wt %.

In the context of a particularly preferred embodiment, an agent is characterized in that it contains—in relation to the total weight of the agent—one or more complexing agents (a) of formula (I) in a total amount of 0.01 to 10.0 wt %, preferably of 0.05 to 7.5 wt %, more preferably of 0.1 to 5.0 wt %, and very particularly preferably of 0.3 to 3.5 wt %.

In the context of another particularly preferred embodiment, an agent is characterized in that it contains—in relation to the total weight of the agent—one or more complexing agents (a) of formula (Ia) in a total amount of 0.01 to 10.0 wt %, preferably of 0.05 to 7.5 wt %, further preferably of 0.1 to 5.0 wt %, and very particularly preferably of 0.3 to 3.5 wt %.

Activator (b)

As a second component, the agent contains at least one activator (b) from the group of amino acids, protein hydrolyzates, and radical scavengers.

An activator is understood to mean a substance which is capable of further improving the performance, and in particular the bleaching power, of the complexing agent (a). Compounds from the group of amino acids, protein hydrolyzates, and radical scavengers exhibit a good effect as activators (b).

A very particularly good performance has been demonstrated by the oxidative color changing agent containing at least one activator (b) from the group of amino acids.

In the context of a further embodiment, a very particularly preferred agent is characterized in that it contains at least one activator (b) from the group of amino acids—preferably from the group of glycine, lysine, arginine, histidine, asparagine, glutamine, cysteine, methionine, tryptophan, serine, alanine, aspartic acid, glutamic acid, isoleucine, leucine, phenylalanine, proline, threonine, tyrosine, and valine.

Preferred, therefore, are agents for oxidatively changing the color of keratin fibers, containing (a) at least one complexing agent of general formula (I)—preferably of formula (Ia),
(b) at least one amino acid from the group of glycine, lysine, arginine, histidine, asparagine, glutamine, cysteine, methionine, tryptophan, serine, alanine, aspartic acid, glutamic acid, isoleucine, leucine, phenylalanine, proline, threonine, tyrosine, and valine, and
(c) at least one oxidant.

An amino acid is understood to mean a chemical compound having an amino group and a carboxylic acid group. The class of amino acids includes organic compounds which contain at least one amino group (—$NH_2$ or substituted —$NR_2$) and a carboxy group (—COOH) as functional groups, i.e., have structural features of amines and carboxylic acids. Chemically, they can differ in the position of their amino group relative to the carboxy group; if the amino group at the $C_\alpha$ atom is directly adjacent to the terminal carboxy group, this is called α-terminal, and reference is made to α-amino acids. Carboxylic acids having a total number of C atoms of C2-C20, more preferably of C2-C15, and particularly preferably of C2-C10, are preferably used.

In the context of a further particularly preferred embodiment, an agent is characterized in that it contains at least one activator (b) from the group of amino acids—preferably from the group of glycine, lysine, arginine, histidine, asparagine, glutamine, cysteine, methionine, tryptophan, serine, alanine, aspartic acid, glutamic acid, isoleucine, leucine, phenylalanine, proline, threonine, tyrosine, and valine.

When the agents are used, a particularly high color shift (i.e., a particularly high delta-E value) can be achieved in comparison with the starting hair if the agents contained at least one amino acid (b) from the group of glycine, lysine, arginine, and valine.

Agents containing at least one amino acid (b) from the group of glycine, lysine, arginine, and valine are therefore very particularly preferred in view of achieving an improved lightening performance.

If the amino acids lysine and/or glycine were used in the agent, the temperature profile occurring during the application could also be influenced quite positively. For this reason, the amino acids of glycine, lysine, arginine, and valine are most preferred.

Explicitly, most of all and very particularly preferred, therefore, are agents for oxidatively changing the color of keratin fibers containing (a) at least one complexing agent of general formula (I)—preferably of formula (Ia),
(b) at least one amino acid from the group of glycine, lysine, arginine, and valine, and
(c) at least one oxidant.

Chiral amino acids have a stereogenic center and can occur in mirror-image forms. For example, arginine occurs in the form of L-arginine and D-arginine. Both the L-form of an amino acid and its D-form and the mixtures thereof are usable herein. Both possible enantiomers can therefore equally be used as a specific compound or else mixtures thereof, and in particular as racemates. However, it is particularly advantageous to use the naturally occurring isomer form, usually in the L configuration.

Accordingly, a particularly preferred agent is characterized in that it contains at least one amino acid (b) from the group of glycine, L-lysine, L-arginine, L-histidine, L-asparagine, L-glutamine, L-cysteine, L-methionine, L-tryptophan, L-serine, L-alanine, L-aspartic acid, L-glutamic acid, L-isoleucine, L-leucine, L-phenylalanine, L-proline, L-threonine, L-tyrosine, and L-valine.

For achieving the best possible results, and in particular good lightening results, the amino acid(s) (b) is/are preferably used in certain quantity ranges. It has proven to be particularly advantageous if the agent contains—in relation to its total weight—one or more amino acids (b) in a total amount of 0.1 to 10.0 wt %, preferably of 0.1 to 5.0 wt %, more preferably of 0.1 to 2.5 wt %, and very particularly preferably of 0.1 to 2.0 wt %.

In the context of another particularly preferred embodiment, an agent is characterized in that it contains—in relation to the total weight of the agent—one or more amino acids (b) in a total amount of 0.1 to 10.0 wt %, preferably 0.1 to 5.0 wt %, further preferably of 0.1 to 2.5 wt %, and very particularly preferably of 0.1 to 2.0 wt %.

Furthermore, good results could be obtained if at least one protein hydrolyzate was used as activator (b).

Protein hydrolyzates are degradation products of proteins which are prepared by acidic, basic, or enzymatic reaction. Due to the preparation process, protein hydrolyzates have a distributed molecular weight. The protein hydrolyzates also include oligopeptides, as these can also be produced from proteins by corresponding reactions. The protein hydrolyzates therefore do not include single amino acids, which are present as a discrete individual compound. Protein hydrolyzates of plant, animal, marine, or synthetic origin can be used.

Protein hydrolyzates are understood to mean at most oligomeric compounds which are composed of a maximum of 10 amino acids.

Animal protein hydrolyzates are, for example, elastin, collagen, keratin, silk, and milk protein hydrolyzates, which can also be present in the form of salts. Such products are marketed, for example, under the trademarks, Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), ProSina® (Croda), and Kerasol® (Croda).

Furthermore, plant protein hydrolyzates such as soybean, almond, pea, moringa, potato, and wheat protein hydrolyzates are preferred. Such products are available, for example, under the trademarks, Gluadin® (Cognis), DiaMin® (Diamalt), Lexein® (Inolex), Hydrosoy® (Croda), Hydrolupin® (Croda), Hydrosesame® (Croda), Hydrotitium® (Croda), Crotein® (Croda), and Puricare® LS 9658 from the company Laboratoires Serobiologiques.

Another very particularly suitable plant protein hydrolyzate is the raw material Gluadin®Kera-P LM, which represents a "hydrolyzed vegetable protein" and can be purchased commercially from BASF, for example.

Further protein hydrolyzates which are preferred are of marine origin. This includes, for example, collagen hydrolyzates from fish or algae and protein hydrolyzates from mussels or pearl hydrolyzates. Examples of pearl extracts are the trade products, Pearl Protein Extract BG® or Crodarom® Pearl.

Furthermore, protein hydrolyzates include cationized protein hydrolyzates, wherein it is possible for the underlying protein hydrolyzate to originate from animals, e.g., from collagen, milk, or keratin, from plants, e.g., from wheat, corn, rice, potatoes, soybeans, or almonds, from marine life forms, e.g., from fish collagen or algae, or from biotechnologically-obtained protein hydrolyzates. Typical examples of cationic protein hydrolyzates and derivatives are the commercially available products known under the INCI names in the "International Cosmetic Ingredient Dictionary and Handbook" (seventh edition 1997, The Cosmetic, Toiletry, and Fragrance Association, 1101 17$^{th}$ Street, N.W., Suite 300, Washington, DC 20036-4702).

Good results could be observed if the agent contained at least one protein hydrolyzate selected from the group of plant protein hydrolyzates, the protein hydrolyzates of elastin, collagen, keratin, silk, milk protein, soy protein hydrolyzates, almond protein hydrolyzates, pea protein hydrolyzates, moringa protein hydrolyzates, potato protein hydrolyzates, and wheat protein hydrolyzates.

In the context of a further particularly preferred embodiment, an agent is characterized in that it contains at least one activator (b) from the group of protein hydrolyzates—preferably from the group of plant protein hydrolyzates, the protein hydrolyzates of elastin, collagen, keratin, silk, milk protein, soy protein hydrolysates, almond protein hydrolysates, pea protein hydrolysates, moringa protein hydrolysates, potato protein hydrolysates, and wheat protein hydrolysates.

Agents which are very particularly preferred in the context of this embodiment are characterized in that they contain (a) at least one complexing agent of general formula (I)—preferably of formula (Ia), (b) at least one protein hydrolyzate from the group of plant protein hydrolyzates, the protein hydrolyzates of elastin, collagen, keratin, silk, milk protein, soy protein hydrolyzates, almond protein hydrolyzates, pea protein hydrolyzates, moringa protein hydrolyzates, potato protein hydrolyzates, and wheat protein hydrolyzates, and (c) at least one oxidant.

In order to achieve the best possible results, and in particular good lightening results, the protein hydrolyzates (b) are preferably used in certain quantity ranges. It has proven to be particularly advantageous if the agent contains—in relation to the total weight of the agent—one or more protein hydrolyzates (b) in a total amount of 0.1 to 10.0 wt %, preferably 0.1 to 5.0 wt %, more preferably of 0.1 to 2.5 wt %, and very particularly preferably of 0.1 to 2.0 wt %.

In the context of another particularly preferred embodiment, an agent is characterized in that it contains—in relation to the total weight of the agent—one or more protein hydrolyzates (b) in a total amount of 0.1 to 10.0 wt %, preferably 0.1 to 5.0 wt %, further preferably of 0.1 to 2.5 wt %, and very particularly preferably of 0.1 to 2.0 wt %.

Oligopeptides are also protein hydrolyzates. Oligopeptides may be preferred in the hair treatment agents owing to their defined amino acid sequence.

An oligopeptide that has at least one amino acid sequence Glu-Glu-Glu,

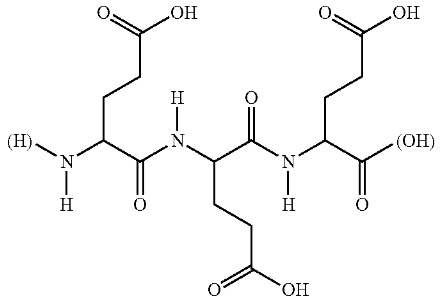

wherein the amino group can be free or protonated and the carboxy group can be free or deprotonated, may be particularly preferred. In this formula, as in all preceding formulas, the bracketed hydrogen atom of the amino group, as well as the bracketed hydroxy group of the acid function, means that the groups in question can be present as such (making it an oligopeptide having the relevant number of amino acids, as in the formula above), or that the amino acid sequence is present in an oligopeptide which also comprises further amino acids; depending upon where the further amino acid(s) is/are bound, the bracketed components of the above-mentioned formula are replaced by the further amino acid functional group(s).

In the context of the present application, oligopeptides are condensation products of amino acids which are linked by peptide bonds in the manner of an acid amide and which comprise at least 3 and at most 25 amino acids. In hair treatment agents which are preferred, the oligopeptide comprises 5 to 15 amino acids, preferably 6 to 13 amino acids, particularly preferably 7 to 12 amino acids, and in particular 8, 9, or 10 amino acids. Depending upon whether further amino acids are bound to the sequence Glu-Glu-Glu and depending upon the type of said amino acids, the molar mass of the oligopeptide contained in the agents may vary. Hair treatment agents which are preferred are characterized in that the oligopeptide has a molar mass of 650 to 3,000 daltons, preferably of 750 to 2,500 daltons, particularly preferably of 850 to 2,000 daltons, and in particular of 1,000 to 1,600 daltons. As can be seen from the preferred number of amino acids in the oligopeptides and the preferred molar mass range, oligopeptides are preferably used which consist not only of the three glutamic acids, but also have additional amino acids bound to this sequence. These further amino acids are preferably selected from certain amino acids, whereas certain other representatives are less preferred. A particularly preferred oligopeptide additionally contains tyrosine, which is preferably bound via its acid function to the sequence Glu-Glu-Glu. Hair treatment agents that are preferred are therefore characterized in that the oligopeptide contained therein has at least one amino acid sequence Tyr-Glu-Glu-Glu,

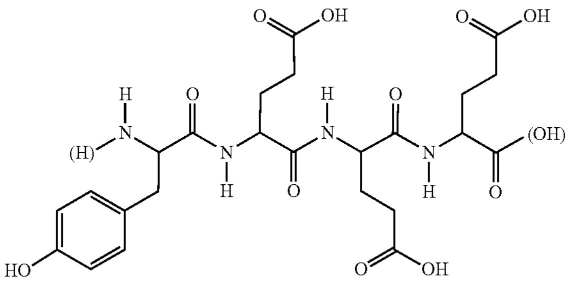

wherein the amino group can be free or protonated, and the carboxyl group can be free or deprotonated.

A further particularly preferred oligopeptide additionally contains isoleucine, which is preferably bound via its amino function to the sequence Glu-Glu-Glu. Hair treatment agents that are preferred are therefore characterized in that the oligopeptide contained therein has at least one amino acid sequence Glu-Glu-Glu-Ile,

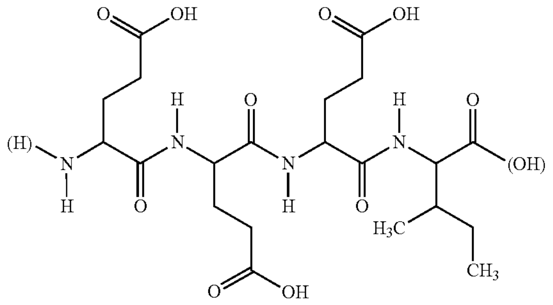

wherein the amino group can be free or protonated, and the carboxyl group can be free or deprotonated.

Oligopeptides that have both of the aforementioned amino acids (tyrosine and isoleucine) are preferred. Here, hair treatment agents that are particularly preferred are those in which the contained oligopeptide contained comprises at least one amino acid sequence Tyr-Glu-Glu-Glu-Ile,

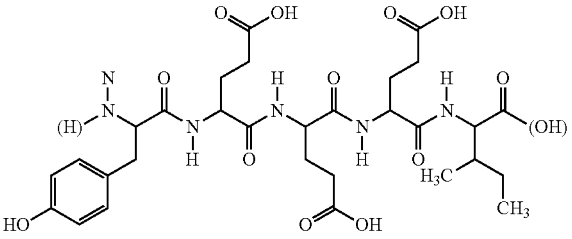

wherein the amino group can be free or protonated, and the carboxyl group can be free or deprotonated.

Further preferred oligopeptides additionally contain arginine, which is preferably present bound to isoleucine.

Still further preferred oligopeptides additionally contain valine, which is preferably present bound to the arginine. Hair treatment agents that are more preferred are therefore characterized in that the oligopeptide contained therein has at least one amino acid sequence Tyr-Glu-Glu-Glu-Ile-Arg-Val

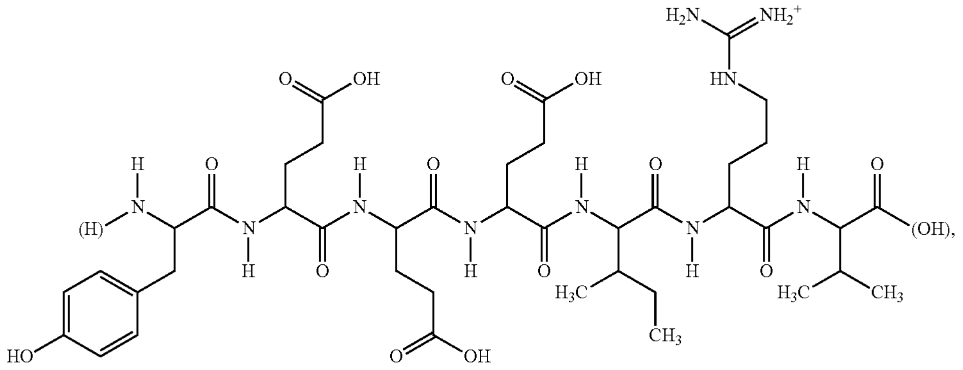

wherein it is possible for the amino groups to be present in a free or protonated form and for the carboxy groups to be present in a free or deprotonated form.

Still further preferred oligopeptides additionally contain leucine, which is preferably present bound to valine. Hair treatment agents which are further preferred are characterized in that the oligopeptide contained therein has at least one amino acid sequence Tyr-Glu-Glu-Glu-Ile-Arg-Val-Leu

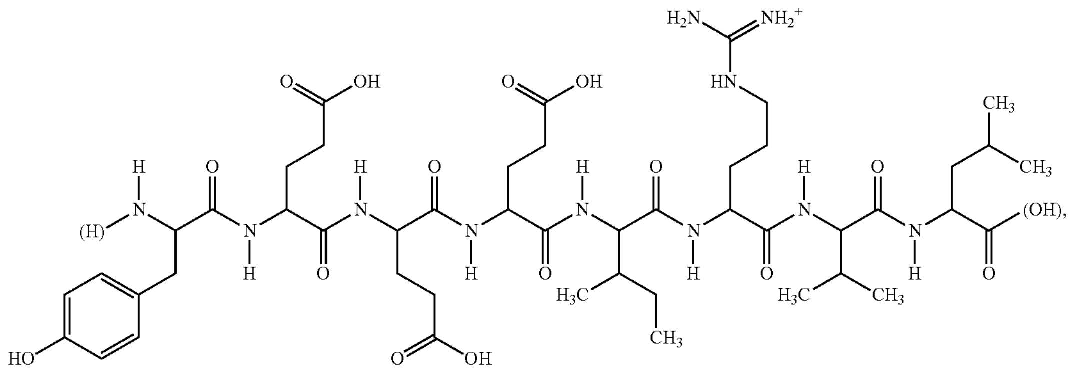

wherein it is possible for the amino groups to be present in a free or protonated form and for the carboxy groups to be present in a free or deprotonated form.

Particularly preferred oligopeptides additionally contain leucine, which is preferably present bound to the tyrosine. Hair treatment agents which are further preferred are characterized in that the oligopeptide contained therein has at least one amino acid sequence Leu-Tyr-Glu-Glu-Glu-Ile-Arg-Val-Leu

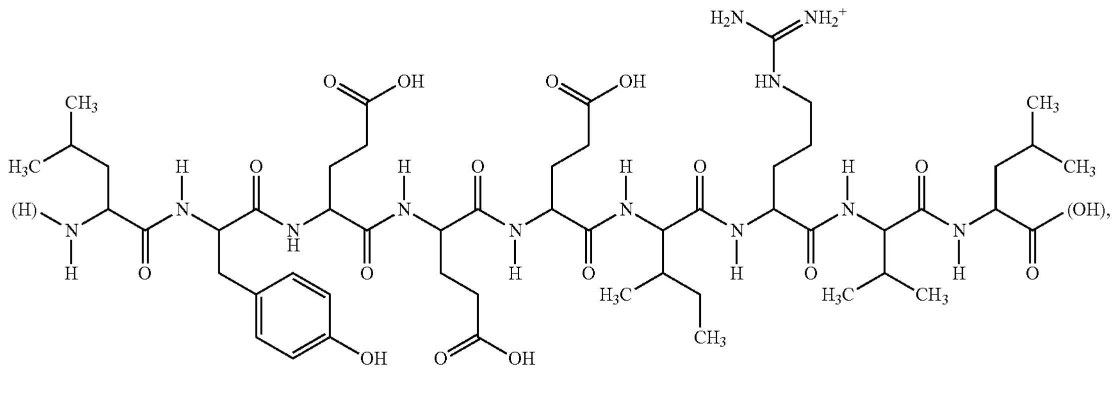

wherein it is possible for the amino group to be present in a free or protonated form and for the carboxy groups to be present in a free or deprotonated form.

In the course of further work, it was found that radical scavengers are also very suitable as activator (b).

A radical scavenger is understood to mean substances which react with reactive radicals, such as hydroxy radicals, and convert these by a series of rapid reactions into less reactive species, thereby interrupting the radical chain reaction.

The radical scavengers suitable for use in cosmetics can be assigned to certain groups. For use in the lightening or bleaching agents, the use in particular of one or more radical scavengers from the group of unsaturated organic compounds, antioxidants, quinones, and thiols has proven to be particularly suitable.

In the context of a further particularly preferred embodiment, an agent is characterized in that it contains at least one activator (b) from the group of radical scavengers—preferably from the group of unsaturated organic compounds, antioxidants, quinones, and thiols.

It has proven to be very particularly preferred, to achieve the object, to use, in the agent, at least one radical scavenger (b) from the group of unsaturated organic compounds. An unsaturated organic compound is understood to mean an organic compound having at least one carbon-carbon double bond.

The use of at least one mono- or polyunsaturated $C_8$-$C_{30}$ fatty acid and/or the derivative of a mono- or polyunsaturated $C_8$-$C_{30}$ fatty acid has been found to be very particularly advantageous.

Unsaturated fatty acids are to be understood as mono- or polyunsaturated, unbranched or branched, unsubstituted or substituted $C_8$-$C_{30}$ carboxylic acids. Unsaturated fatty acids may be mono-unsaturated or poly-unsaturated. With an unsaturated fatty acid, the C—C double bond(s) thereof may have the cis or trans configuration.

In the context of a further very particularly preferred embodiment, an agent is characterized in that it contains at least one radical scavenger (b) from the group of unsaturated $C_8$-$C_{30}$ fatty acids and derivatives thereof.

Examples of an unsaturated $C_8$-$C_{30}$ fatty acid are petroselic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z, 15Z)-octadeca-9,12,15-trienoic acid, elaeostearic acid [(9Z, 11E, 13E)-octadeca-9,11,3-trienoic acid], arachidonic acid [(5Z, 8Z, 11Z, 14Z)-icosa-5,8,11,14-tetraenoic acid] and/or nervonic acid [(15Z)-tetracos-15-enoic acid]. Very particularly preferred unsaturated $C_8$-$C_{30}$ fatty acids are linoleic acid [(9Z, 12Z)-octadeca-9,12-dienoic acid, linolenic acid [(9Z, 12Z,15Z)-octadeca-9,12,15-trienoic acid.

In a further particularly preferred embodiment, an agent is characterized in that it contains at least one radical scavenger (b), which is selected from the group of petroselic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid]. Very particularly preferred unsaturated $C_8$-$C_{30}$ fatty acids are linoleic acid [(9Z, 12Z)-octadeca-9,12-dienoic acid, linolenic acid [(9Z,12Z,15Z)-octadeca-9,12,15-trienoic acid.

Examples of very particularly well-suited unsaturated $C_8$-$C_{30}$ fatty acids are linoleic acid and linolenic acid. These are essential fatty acids which are also known in the literature under the name vitamin F.

In a further very particularly preferred embodiment, an agent is characterized in that it contains at least one radical scavenger (b), which is selected from the group of linoleic acid and linolenic acid.

Particularly well-suited derivatives of $C_8$-$C_{30}$ fatty acids are their esters.

Characteristic for an ester of an unsaturated $C_8$-$C_{30}$ fatty acid is the presence of a functional ester group obtained by esterification of the acid function of the fatty acid with an alcohol. This alcohol may be a monovalent alcohol or polyvalent alcohol which may optionally also bear further functional groups or substituents.

Examples of monovalent alcohols are methanol, ethanol, n-propanol, iso-propanol, n-butanol, n-pentanol, n-hexanol, n-heptanol, n-octanol, n-nonanol, n-decanol, n-undecanol, n-dodecanol, n-tetradecanol, n-hexadecanol, and n-octadecanol.

Examples of polyvalent alcohols are 1,2-propanediol, 1,3-propanediol, and glycerol. Glycerol is particularly preferred.

Further examples of the esters of unsaturated $C_8$-$C_{30}$ fatty acids are corresponding fatty acid monoglycerides, fatty acid diglycerides, and fatty acid triglycerides.

A $C_8$-$C_{30}$ fatty acid monoglyceride is understood to mean the monoester of the trivalent alcohol, glycerol, with an unsaturated $C_8$-$C_{30}$ fatty acid equivalent. In this case, either the middle hydroxy group of glycerol or the terminal hydroxy group of glycerol may be esterified with a fatty acid.

The $C_{12}$-$C_{30}$ fatty acid monoglycerides are characterized by particular suitability, in which a hydroxy group of the glycerol is esterified with a fatty acid, wherein the fatty acids are selected from petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5, 8,11,14-tetraenoic acid], or nervonic acid [(15Z)-tetracos-15-enoic acid].

A $C_{12}$-$C_{30}$ fatty acid diglyceride is understood to mean the diester of the trivalent alcohol, glycerol, with two $C_8$-$C_{30}$ fatty acid equivalents, wherein at least one fatty acid must be an unsaturated $C_8$-$C_{30}$ fatty acid. In this case, either the middle and a terminal hydroxy group of glycerol can be esterified with two fatty acid equivalents, or, instead, both terminal hydroxy groups of glycerol are each esterified with one fatty acid. The glycerol here can be esterified both with two structurally identical and with two different fatty acids, wherein there is the proviso that at least one fatty acid be an unsaturated $C_8$-$C_{30}$ fatty acid.

The fatty acid diglycerides are characterized by particular suitability, in which at least one of the ester groups is formed starting from glycerol with a fatty acid which is selected from petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5, 8,11,14-tetraenoic acid], or nervonic acid [(15Z)-tetracos-15-enoic acid].

A $C_{12}$-$C_{30}$ fatty acid triglyceride is understood to mean the triester of the trivalent alcohol, glycerol, with three $C_8$-$C_{30}$ fatty acid equivalents, wherein at least one fatty acid must be an unsaturated $C_8$-$C_{30}$ fatty acid. The glycerol here can be esterified both with three structurally identical and with different fatty acids, wherein there is the proviso that at least one fatty acid be an unsaturated $C_8$-$C_{30}$ fatty acid.

The fatty acid triglycerides are characterized by particular suitability, in which at least one of the ester groups is formed starting from glycerol with a fatty acid which is selected from petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5, 8,11,14-tetraenoic acid], or nervonic acid [(15Z)-tetracos-15-enoic acid].

The radical scavengers (b) from the group of phosphoglycerides have been found to be explicitly very particularly suitable for achieving the object. Phosphoglycerides fall under the group of esters of $C_8$-$C_{30}$ fatty acids.

Phosphoglycerides are understood in this context to mean substances which can alternatively also be referred to as glycerophospholipids/phosphoglycerolipids.

Phosphoglycerides are constructed from glycerol which is esterified with two $C_8$-$C_{30}$ fatty acids at two of the hydroxy groups (OH groups) of the glycerol, wherein there is the proviso that at least one fatty acid be an unsaturated $C_8$-$C_{30}$ fatty acid. A phosphate group is bound to one of the third, terminal OH groups. This phosphate group is in turn esterified with different alcohols. The phosphate group forms a phosphoric diester.

The radical scavengers (b) from the group of lecithins are explicitly very particularly preferred.

In the context of another explicitly very particularly preferred embodiment, an agent is characterized in that it contains at least one radical scavenger (b) of general formula (II),

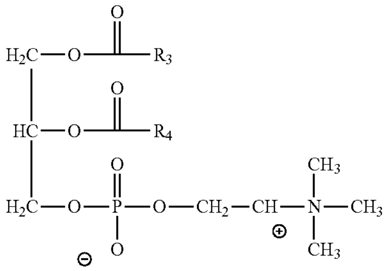

(II)

where

R3, R4, independently of one another, represent a saturated or unsaturated $C_{11}$-$C_{29}$ alkyl group, with the proviso that at least one of the groups from R3 and R4 represent an unsaturated $C_{11}$-$C_{29}$ alkyl group.

The groups R3 and/or R4 may preferably represent the following groups. Together with the carbonyl group adjacent to the group R3 or R4, this group forms the esterified form of the fatty acid stated in the table from:

| Fatty acid | R3 and/or R4 |
| --- | --- |
| petroselinic acid [(Z)-6-octadecenoic acid]. | 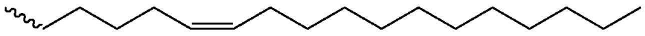 monounsaturated $C_{17}$ alkyl group |
| palmitoleic acid [(9Z)-hexadec-9-enoic acid] | 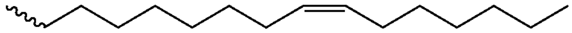 monounsaturated $C_{15}$ alkyl group |
| oleic acid [(9Z)-octadec-9-enoic acid] | 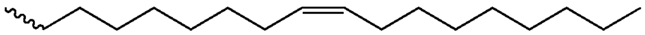 monounsaturated $C_{17}$ alkyl group |
| elaidic acid [(9E)-octadec-9-enoic acid] | 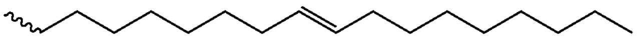 monounsaturated $C_{17}$ alkyl group |
| erucic acid [(13Z)-docos-13-enoic acid] | 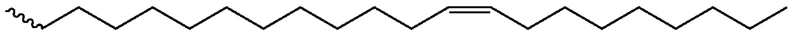 monounsaturated $C_{21}$ alkyl group |
| linoleic acid [(9Z, 12Z)-octadeca-9,12-dienoic acid | 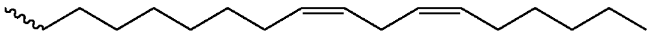 diunsaturated $C_{17}$ alkyl group |
| Linolenic acid [(9Z, 12Z, 15Z)-octadeca-9,12,15-trienoic acid | 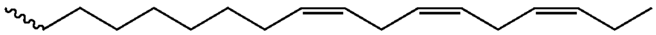 triunsaturated $C_{17}$ alkyl group |
| elaeostearic acid [(9Z,11E,13E)-octadeca-9,11,3-trienoic acid] | 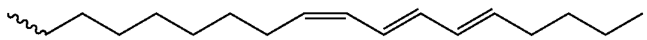 triunsaturated $C_{17}$ alkyl group |
| arachidonic acid [(5Z, 8Z, 11Z, 14Z)-icosa-5,8,11,14-tetraenoic acid] | 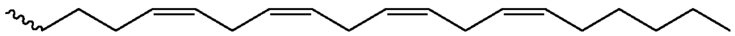 4-fold unsaturated C19 alkyl group |
| nervonic acid [(15Z)-tetracos-15-enoic acid] | 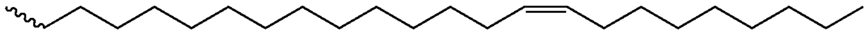 monounsaturated $C_{23}$ alkyl group |

Preferably, at least one of the groups R3 and/or R4 represents an at least monounsaturated $C_{16}$-$C_{20}$ alkyl group, particularly preferably an at least diunsaturated $C_{16}$-$C_{20}$ alkyl group, and explicitly very particularly preferably an at least triunsaturated $C_{16}$-$C_{20}$ alkyl group.

In the context of a further explicitly very particularly preferred embodiment, an agent is characterized in that it contains at least one radical scavenger (b) of general formula (II), wherein at least one of the groups R3 and/or R4 represents an at least monounsaturated $C_{15}$-$C_{21}$ alkyl group, particularly preferably an at least diunsaturated $C_{15}$-$C_{21}$ alkyl group, and explicitly very particularly preferably an at least triunsaturated $C_{15}$-$C_{21}$ alkyl group.

linoleic acid [(9Z, 12Z)-octadeca-9,12-dienoic acid

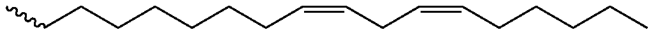

diunsaturated $C_{17}$ alkyl group linolenic acid [(9Z,12Z,15Z)-octadeca-9,12,15-trienoic acid

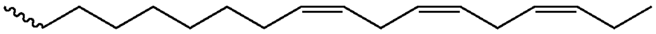

triunsaturated $C_{17}$ alkyl group

In the context of a further explicitly very particularly preferred embodiment, an agent is characterized in that it contains at least one radical scavenger (b) of the general formula (II), where at least one of the radicals R3 and/or R4 is a diunsaturated $C_{17}$ alkyl group or a triunsaturated $C_{17}$ alkyl group.

If one of the remaining groups R3 or R4 represents a saturated $C_{11}$-$C_{29}$ alkyl group, this group may preferably be a saturated $C_{11}$ alkyl group, a saturated $C_{13}$ alkyl group, a saturated $C_{15}$ alkyl group, a saturated $C_{17}$ alkyl group, a saturated $C_{19}$ alkyl group or a saturated $C_{21}$ alkyl group.

As explicitly very particularly suitable lecithin of formula (II), soybean lecithin can be used, which is commercially available under the trade name, Lipoid P20, from Lipoid GmbH. This raw material has a content of phosphatidyl choline(=lecithin) of at least 20 wt %, wherein at least 61 wt % of the fatty acids—in relation to the total content of the fatty acids obtained after the hydrolysis of the lecithin—is linoleic acid or linolenic acid.

Agents which are very particularly preferred in the context of this embodiment are characterized in that they contain (a) at least one complexing agent of general formula (I)—preferably of formula (Ia),
(b) at least one radical scavenger of general formula (II), and
(c) at least one oxidant.

From the group of antioxidants, vitamin F, vitamin E, vitamin C, vitamin A, vitamin B, and vitamin H have been found to be highly suitable as radical scavenger (b).

Vitamin F: The term, vitamin F, is usually understood as meaning essential fatty acids, and in particular linoleic acid, linolenic acid, as already described above.

Vitamin E: Vitamin E is a collective term for fat-soluble substances with usually antioxidative effects. The most frequently occurring vitamin E forms are called tocopherols and tocotrienols. As particularly suitable vitamin E, α-tocopherol can be used. Alternatively, α-tocopherol is also referred to as (2R)-2,5,7,8-tetramethyl-2-[(4R,8R)-4,8,12-trimethyltridecyl]-3,4-dihydro-2H-chromen-6-ol or as E 307, and bears the CAS number 10191-41-0.

The group of substances designated as vitamin A includes retinol (vitamin $A_1$) and 3,4-didehydroretinol (vitamin $A_2$). β-carotin is the provitamin of retinol. As vitamin A components, mention may be made of, for example, vitamin A acid and esters thereof, vitamin A aldehyde and vitamin A alcohol, and esters thereof such as the palmitate and acetate.

Vitamin C (ascorbic acid) and its esters—in particular, ascorbyl palmitate—are also suitable.

The vitamin B group or vitamin B-complex includes, inter alia, vitamin $B_1$ (thiamine)
vitamin $B_2$ (riboflavin)
vitamin $B_3$. This designation often includes the compounds, nicotinic acid and nicotinamide (niacinamide), among which, in particular, nicotinamide is preferred.
vitamin $B_5$ (panthothenic acid and panthenol). Panthenol is preferably used in the context of this group. Derivatives of panthenol which can be used are in particular the esters and ethers of panthenol as well as cationically-derivatized panthenols and pantolactone.
vitamin $B_6$ (pyridoxine as well as pyridoxamine and pyridoxal).

Vitamin H. The compound (3aS,4S, 6aR)-2-oxohexahydrothienol[3,4-d]-imidazol-4-valeric acid is designated as vitamin H, for which the trivial name, biotin, has become accepted.

In the context of a further preferred embodiment, an agent is characterized in that it contains at least one radical scavenger (b) from the group of vitamin F, vitamin E, vitamin C, vitamin A, vitamin B, and vitamin H.

In the context of a further particularly preferred embodiment, an agent is characterized in that it contains at least one radical scavenger (b) from the group of vitamin F, vitamin E, vitamin C, and vitamin A.

Further suitable radical scavengers (b) are compounds from the group of quinones. Quinones are understood to mean organic compounds which have a quinoid system. Suitable representatives from the group of quinones are 1,4-benzoquinone, 1,4-napthoquinone, 2-hydroxy-1,4-napthoquinone. 1,4-benzoquinones and 1,4-napthoquinones, such as at least one substituent such as a hydroxy group, an amino group, a nitro group, a carboxylic acid group, a $C_1$-$C_6$ alkyl group, a $C_1$-$C_6$ alkoxy group, are also suitable.

Examples of suitable radical scavengers (b) from the group of thiols are thiolactic acid, ammonium thioglycolate, and ammonium thiolactate.

Thiolactic acid is understood to mean D-thiolactic acid, L-thiolactic acid, and/or the mixture thereof. Cysteine is understood to mean D-cysteine, L-cysteine, and/or the mixture thereof.

Ammonium thioglycolate is the ammonium salt of thiglycolic acid (i.e., the ammonium salt of sulfanylacetic acid) (formula thiol-I)

(formula thiol-I)

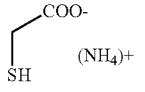

Ammonium thiolactate is the ammonium salt of thiolactic acid (i.e., the ammonium salts of 2-sulfanylpropionic acid) (formula thiol-II).

(formula thiol-II)

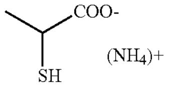

The definition of ammonium thiolactate includes the ammonium salts of D-thiolactic acid and also the salts of L-thiolactic acid, and the mixtures thereof.

To optimize the desired effect, the radical scavengers (b) are also preferably used in certain quantity ranges in the agent.

It has proven to be very particularly advantageous if the agent contains—in relation to the total weight of the agent—one or more radical scavengers (b) in a total amount of 0.01 to 10.0 wt %, preferably 0.25 to 7.0 wt %, more preferably of 0.25 to 5.0 wt %, and very particularly preferably of 0.25 to 3.5 wt %.

In the context of another very particularly preferred embodiment, an agent is therefore characterized in that it contains—in relation to the total weight of the agent—one or more protein radical scavengers (b) in a total amount of 0.01 to 10.0 wt %, preferably 0.25 to 7.0 wt %, further preferably of 0.25 to 5.0 wt %, and very particularly preferably of 0.25 to 3.5 wt %.

Weight Ratio (a)/(b)

The work has shown that a synergistic effect appears to exist between components (a) and (b). When both components (a) and (b) are used in an agent for oxidative color change, it has been shown that (a) and (b) together very particularly strongly improve the lightening performance when they are present in the agent in a certain weight ratio.

For this reason, it has been found to be very particularly preferred if the weight ratio of all the complexing agents (a) of the formula (I) present in the agent to all activators (b) contained in the agent, i.e., the weight ratio (a)/(b), is of a value of 0.1 to 10, preferably of 0.2 to 5, further preferably of 0.25 to 4.0, and very particularly preferably of 0.3 to 1.0.

In the context of a further preferred embodiment, an agent is characterized in that the weight ratio of all the complexing agents (a) contained in the agent to all the activators (b) contained in the agent, i.e., the weight ratio (a)/(b), has a value of 0.1 to 10, preferably of 0.2 to 5, more preferably of 0.25 to 4.0, and very particularly preferably of 0.3 to 1.0.

It is preferred if the weight ratio of all the complexing agents (a) contained in the agent to all the amino acids (b) contained in the agent, i.e., the weight ratio (a)/(b), has a value of 0.1 to 10, preferably of 0.2 to 5, more preferably of 0.25 to 4.0, and very particularly preferably of 0.3 to 1.0.

It is preferred if the weight ratio of all the complexing agents (a) contained in the agent to all the protein hydrolyzates (b) contained in the agent, i.e., the weight ratio (a)/(b), has a value of 0.1 to 10, preferably of 0.2 to 5, more preferably of 0.25 to 4.0, and very particularly preferably of 0.3 to 1.0.

It is preferred if the weight ratio of all complexing agents (a) present in the agent to all radical scavengers (b) contained in the agent, i.e., the weight ratio (a)/(b), is of a value of 0.1 to 10, preferably of 0.2 to 5, more preferably of 0.25 to 4.0, and very particularly preferably of 0.3 to 1.0.

Agents for Lightening Keratin Fibers with Oxidants (c)

The combination of the ingredients (a) and (b) shows its potential in agents for oxidatively changing the color, and in particular for lightening or for bleaching, of hair. For this reason, the agent contains at least one oxidant (c) as a third component.

An oxidant is understood by a person skilled in the art to mean a substance or a compound which can oxidize other substances and is thereby reduced itself. Oxidants can absorb electrons, while reducing agents deliver electrons. Oxidants customary in hair treatment can be selected from the group of inorganic and/or organic peroxo compounds.

In order to achieve moderate lightening effects, hydrogen peroxide is the oxidant of choice. Agents preferred as bleaching and decolorizing agents are furthermore characterized in that they contain hydrogen peroxide and/or one of its solid addition products to organic or inorganic compounds. However, if a stronger lightening or bleaching is desired, hydrogen peroxide is used together with stronger oxidants such as persulfates (sodium persulfate, potassium persulfate, or ammonium persulfate).

In the context of a particularly preferred embodiment, an agent is characterized in that it contains (c) at least one oxidant from the group of hydrogen peroxide, ammonium peroxodisulfate, potassium peroxodisulfate, and sodium peroxodisulfate.

In this embodiment, particularly preferred therefore is an agent for oxidatively changing the color of keratin fibers, and in particular human hair, containing in a cosmetic carrier (a) at least one complexing agent of general formula (I)—preferably of formula (Ia), (b) at least one amino acid, and (c) at least one oxidant from the group of hydrogen peroxide, ammonium peroxodisulfate, potassium peroxodisulfate, and sodium peroxodisulfate.

In this embodiment, particularly preferred therefore is an agent for oxidatively changing the color of keratin fibers, and in particular human hair, containing in a cosmetic carrier (a) at least one complexing agent of general formula (I)—preferably of formula (Ia), (b) at least one protein hydrolyzate, and (c) at least one oxidant from the group of hydrogen peroxide, ammonium peroxodisulfate, potassium peroxodisulfate, and sodium peroxodisulfate.

In this embodiment, particularly preferred therefore is an agent for oxidatively changing the color of keratin fibers, and in particular human hair, containing in a cosmetic carrier (a) at least one complexing agent of general formula (I)—preferably of formula (Ia), (b) at least one radical scavenger, and (c) at least one oxidant from the group of hydrogen peroxide, ammonium peroxodisulfate, potassium peroxodisulfate, and sodium peroxodisulfate.

Ammonium peroxodisulfate, which can alternatively also be referred to as ammonium persulfate, is understood to mean the persulfate with the molecular formula $(NH_4)_2S_2O_8$.

Potassium peroxodisulfate, which can alternatively also be referred to as potassium persulfate, is the persulfate with the molecular formula $K_2S_2O_8$.

Sodium peroxodisulfate, which can alternatively also be referred to as sodium persulfate, is understood to mean the persulfate with molecular formula $Na_2S_2O_8$.

In the context of a particularly preferred embodiment, an agent is characterized in that it contains (c1) hydrogen peroxide and (c2) at least one persulfate from the group of ammonium peroxodisulfate, potassium peroxodisulfate, and sodium peroxodisulfate.

In a further preferred embodiment hydrogen peroxide itself is used as an aqueous solution. The concentration of a hydrogen peroxide solution in the agent is determined by the legal requirements, on one hand, and by the desired effect, on the other; preferably, 3 to 12 wt % solutions in water are used. Agents forming the first subject matter that are preferred are characterized in that they contain, in relation to the total weight of the agent, (a) 0.1 to 12.0 wt %, preferably 0.5 to 10.5 wt %, more preferably 1.0 to 8.5 wt %, even more preferably of 1.5 to 7.0 wt %, and very particularly preferably of 1.5 to 6.0 wt %, hydrogen peroxide.

In the context of a particularly preferred embodiment, an agent is characterized in that it contains—in relation to the total weight of the agent—(c) 0.1 to 12.0 wt %, preferably 0.5 to 10.5 wt %, more preferably 1.0 to 8.5 wt %, even more preferably of 1.5 to 7.0 wt %, and very particularly preferably 1.5 to 6.0 wt %, hydrogen peroxide.

Preferably, the one or more persulfates are used in certain ranges of amounts in the agent. It has proven to be preferable if the agent contains—in relation to the total weight of the agent—(c) one or more persulfates from the group of ammonium peroxodisulfate, potassium peroxodisulfate, and sodium peroxodisulfate, in a total amount of 2.0 to 40.0 wt %, preferably of 4.0 to 30.0 wt %, more preferably of 6.0 to 20.0 wt %, and very particularly preferably of 8.0 to 15.0 wt %.

In the context of a particularly preferred embodiment, an agent is characterized in that it contains—in relation to the total weight of the agent—(c) one or more persulfates from the group of ammonium peroxodisulfate, potassium peroxodisulfate, and sodium peroxodisulfate, in a total amount of 2.0 to 40.0 wt %, preferably of 4.0 to 30.0 wt %, more preferably of 6.0 to 20.0 wt %, and very particularly preferably of 8.0 to 15.0 wt %.

In the context of this embodiment, particularly preferred therefore is an agent for oxidatively changing the color of keratin fibers, and in particular human hair, containing in a cosmetic carrier (a) at least one complexing agent of general formula (I)—preferably of formula (Ia),
(b) at least one amino acid and/or a protein hydrolyzate, and
(c1) 1.5 to 6.0 wt % hydrogen peroxide, and
(c2) one or more persulfates from the group of ammonium peroxodisulfate, potassium peroxodisulfate, and sodium peroxodisulfate in a total amount of 8.0 to 15.0 wt %, wherein all quantities specified in wt % are in relation to the total weight of the agent.

Alkalizing Agent

As already described above, the agent forming the first subject matter is a ready-to-use agent for oxidatively changing the color of keratin fibers—for example, a ready-to-use bleaching or lightening agent. In order to achieve a sufficient bleaching or lightening effect, such agents are usually set to be alkaline to strongly alkaline. High pH values of this kind are necessary to ensure an opening of the outer cuticle layer (cuticula) and thus enable a penetration of the active species (hydrogen peroxide and persulfates) into the hair.

For this reason, it has been found to be very particularly preferred if the agent additionally contains at least one alkalizing agent.

In the context of a further preferred embodiment, an agent is characterized in that it contains at least one alkalizing agent.

Preferred alkalizing agents are, for example, ammonia, alkanolamines, basic amino acids, as well as inorganic alkalizing agents such as alkali/alkaline earth metal hydroxides, alkali/alkaline earth metal metasilicates, alkali/alkaline earth metal silicates, alkali/alkaline earth metal phosphates, and alkali/alkaline earth metal hydrogen phosphates. Lithium, sodium, and/or potassium preferably serve as metal ions. Preferred alkalizing agents are alkali/alkaline earth metal metasilicates and alkali/alkaline earth metal silicates.

Suitable inorganic alkalizing agents are preferably selected from sodium hydroxide, potassium hydroxide, calcium hydroxide, barium hydroxide, sodium phosphate, potassium phosphate, sodium silicate, potassium silicate, magnesium silicate, sodium carbonate, and potassium carbonate. Sodium hydroxide and/or potassium hydroxide are particularly preferred.

Alkanolamines as alkalizing agents are preferably selected from alkanolamines of primary, secondary, or tertiary amines having a $C_2$-$C_6$ alkyl basic structure that carries at least one hydroxy group. Particularly preferred alkanolamines are selected from the group formed by 2-aminoethan-1-ol (monoethanolamine), 3-aminopropan-1-ol, 4-aminobutan-1-ol, 5-aminopentan-1-ol, 1aminopropan-2-ol (monoisopropanolamine), 1-aminobutan-2-ol, 1-aminopentan-2-ol, 1-aminopentan-3-ol, 1-aminopentan-4-ol, 2-amino-2-methylpropanol, 2-amino-2-methylbutanol, 3amino-2-methylpropan-1-ol, 1-amino-2-methylpropan-2-ol, 3-aminopropane-1,2-diol, 2-amino-2-methylpropane-1,3-diol, 2-amino-2-ethyl-1,3-propanediol, N,N-dimethylethanolamine, methylglucamine, triethanolamine, diethanolamine, and triisopropanolamine. Particularly preferred alkanolamines are monoethanolamine, 2-amino-2-methylpropanol, and triethanolamine.

Basic amino acids as alkalizing agent are preferably selected from the group that is constituted from L-arginine, D-arginine, D/L-arginine, L-lysine, D-lysine, D/L-lysine, L-ornithine, D-ornithine, D/L-ornithine, L-histidine, D-histidine, and/or D/L-histidine. L-arginine, D-arginine, and/or D/L-arginine are particularly preferably used as an alkalizing agent. In the context of this embodiment, a basic amino acid can be used as ingredient (b), which—in combination with complexing agent (a)—brings about an improvement in lightening performance and is also responsible for setting the particularly well-suited alkaline pH values.

Particularly well-suited agents have a pH value in the range of 7.5 to 11.5, preferably of 8.0 to 11.5, further preferably of 8.5 to 11.5, and quite particularly preferably of 9.0 to 11.0. The pH values have been measured at a temperature of 22° C. The pH value can be measured, for example, using a commercially available glass electrode.

In the context of a particularly preferred embodiment, an agent is characterized in that it contains water and has a pH value of 7.5 to 11.5, preferably of 8.0 to 11.5, further preferably of 8.5 to 11.5, and very particularly preferably of 9.0 to 11.0.

Omission of HEDP or EDTA

The aim of the present application is, in particular, to dispense with the biologically non-degradable complexing agents HEDP and EDTA. For this reason, the agents contain these two complexing agents preferably in particularly small amounts. Very particularly preferably, the agents are free of these two substances. The agent is very particularly preferably also substantially free of the salts of HEDP and EDTA.

In the context of a further preferred embodiment, an agent is characterized in that—in relation to the total weight of the agent—the total content of the substances, contained in the agent, from the group of etidronic acid and the salts of etidronic acid is below 0.2 wt %, preferably below 0.1 wt %, further preferably below 0.05 wt %, and very particularly preferably below 0.001 wt %.

In the context of a further preferred embodiment, an agent is characterized in that—in relation to the total weight of the agent—the total content of the substances, contained in the agent, from the group of EDTA and the salts of EDTA is below 0.2 wt %, preferably below 0.1 wt %, more preferably below 0.05 wt %, and very particularly preferably below 0.001 wt %

Etidronic acid is alternatively also referred to as hydroxy-ethane-1,1-diphosphonic acid and bears the CAS number 2809-21-4.

EDTA is alternatively also referred to as ethylenediamine tetraacetate or ethylenediamine tetraacetic acid and bears the CAS numbers 6381-92-6 and 139-33-3 (anhydrous).

Further Ingredients

In addition to the ingredients (a), (b), and (c)—as well as, optionally, the alkalizing agents—the agent can also contain further active ingredients and auxiliary substances as non-mandatory constituents. These will be described hereafter.

Thus, the agents can also contain further active ingredients, auxiliary substances, and additives, such as solvents, fatty constituents such as $C_8$-$C_{30}$ fatty alcohols, $C_8$-$C_{30}$ fatty acid triglycerides, $C_8$-$C_{30}$ fatty acid monoglycerides, $C_8$-$C_{30}$ fatty acid diglycerides and/or hydrocarbons; non-ionic surfactant, anionic surfactants, cationic surfactants, amphoteric and/or zwitterionic surfactants, polymers; structurants such as glucose, maleic acid and lactic acid, hair-conditioning compounds such as phospholipids, e.g., lecithin and cephalins; perfume oils, dimethyl isosorbide, and cyclodextrins; fiber-structure-improving active ingredients—in particular, mono-, di-, and oligosaccharides, such as glucose, galactose, fructose, fruit sugar, and lactose; dyes for coloring the agent; anti-dandruff active ingredients such as piroctone olamine, zinc omadine, and climbazole; vegetable oils; light protection agents and UV blockers; active ingredients such as panthenol, pantothenic acid, pantolactone, allantoin, pyrrolidinone carboxylic acids and their salts, as well as bisabolol; polyphenols—in particular, hydroxycinnamic acids, 6,7-dihydroxycoumarins, hydroxybenzoic acids, plant extracts; fats and waxes such as fatty alcohols, beeswax, montan wax, and paraffins; swelling and penetrating agents such as glycerol, propylene glycol monoethyl ether, carbonates, hydrogen carbonates, guanidines, ureas, and primary, secondary and tertiary phosphates; opacifiers such as latex, styrene/PVP, and styrene/acrylamide copolymers; pearlescent agents such as ethylene glycol mono- and distearate, as well as PEG-3-distearate; oxidation dye precursors, direct dyes, as well as blowing agents such as propane-butane mixtures, $N_2O$, dimethyl ether, $CO_2$, and air.

The selection of these additional substances is made by the person skilled in the art according to the desired properties of the agents. With regard to other facultative components and the employed amounts of said components, reference is made expressly to relevant handbooks known to the person skilled in the art. The additional active ingredients and auxiliaries are used in the preparations preferably in each case in amounts of 0.0001 to 25 wt %, and in particular of 0.0005 to 15 wt %, in relation to the total weight of the particular agent.

Method for Oxidatively Changing the Color of Keratin Fibers

As already described above, the agent forming the first subject matter represents an agent for oxidatively changing the color of keratin fibers. The agent is very particularly preferably a lightening or bleaching agent. This lightening or bleaching agent represents a ready-to-use agent. Accordingly, the agents can be used in a method for oxidatively changing the color of, and in particular for lightening, keratin fibers.

A second subject matter is a method for oxidatively changing the color of keratin fibers, and in particular human hair, wherein an agent as has been disclosed in detail in the description of the first subject matter is applied to the keratin fibers and rinsed out again after a contact time.

Oxidants such as hydrogen oxide and persulfates represent highly reactive compounds which—particularly in an alkaline environment—have only a limited stability. For this reason, the ready-to-use bleaching agent is usually produced shortly before application by mixing two or more separately packaged preparations.

Usually, the oxidants (c) and the alkalizing agents are packaged separately from one another. Various types of packaging are now conceivable for the complexing agent (a) and the activators (b).

Thus, complexing agents (a) and activator (b) can be packaged, for example, together with one or more persulfates, and separately from the hydrogen peroxide. This embodiment is particularly preferred when only two different preparations are to be mixed with one another to produce the ready-to-use agent.

In a preferred embodiment, a method for oxidatively changing the color of keratin fibers is characterized in that at least two preparations (A) and (B) packaged separately from one another are mixed to form a mixture for use, which is applied to the fibers and rinsed again after a contact time, wherein

- preparation (A) contains hydrogen peroxide (c1), and
- preparation (B) contains
  - at least one complexing agent (a) of general formula (I), and
  - at least one activator (b), and
  - at least one persulfate (c2) from the group of ammonium peroxodisulfate, potassium peroxodisulfate, and sodium peroxodisulfate,
- wherein the complexing agent (a) and the activator (b) have already been disclosed in detail in the description of the first subject matter.

The preparations (A) and (B) can be mixed either just with one another or with further, separately packaged preparations immediately prior to application so as to provide a mixture for use.

If three different preparations are to be mixed with one another to produce the ready-to-use agent, it may be preferred to provide the first oxidant with hydrogen peroxide (c1) separately in a first preparation (A), to provide the persulfates (c2) as a second oxidant separately in a second preparation (B), and to further provide a third preparation (C) which contains complexing agents (a) and activator (b).

In a further preferred embodiment, a method for oxidatively changing the color of keratin fibers is characterized in that at least three preparations (A) and (B) and (C) packaged separately from one another are mixed to form a mixture for use, which is applied to the fibers and rinsed again after a contact time, wherein

- preparation (A) contains hydrogen peroxide (c1), and
- preparation (B) contains at least one persulfate (c2) from the group of ammonium peroxodisulfate, potassium peroxodisulfate, and sodium peroxodisulfate, and
- preparation (C) contains at least one complexing agent (a) of general formula (I) and at least one activator (b),
- wherein the complexing agent (a) and the activator (b) have already been disclosed in detail in the description of the first subject matter.

Preparations (B) which contain the persulfates are preferably in powder form. Powders consisting of solid constituents having different particle sizes can be used. It can usually be preferred, however, if the powders exhibit the most homogeneous possible particle size—in particular, in order to facilitate uniform dispersion or dissolution of the powders in the preparations (B).

Furthermore, preparations (B) can also contain the persulfates in a solid cosmetic carrier. A solid cosmetic carrier can contain salts of silicic acid, and in particular salts of silicates and metasilicates with ammonium, alkali metals, and alkaline earth metals. Metasilicates in particular, which, in accordance with the formula $(SiO_2)_n(M_2O)_m$, where M represents an ammonium ion, an alkali metal, or half a stoichiometric equivalent of an alkaline earth metal, are notable for a ratio between n and m of ≤1 and can be construed as chain-like polymeric structures of the $[SiO_3]^{2-}$ anion, can preferably be used. Sodium metasilicate of the formula $[Na_2SiO_3]^{\infty}$, is particularly preferred in this context. Such silicates, which are formed from a silicate of formula $(SiO_2)_n(Na_2O)_m(K_2O)_P$, where n represents a positive rational number, and m and p, independently of one another, represent a positive rational number or 0, with the proviso that at least one of the parameters m or p be different from 0, and the ratio between n and the sum of m and p be between 2:1 and 4:1, are likewise preferred.

The solid preparations (B) can furthermore contain what are known as pouring aids, which are intended to prevent clumping or caking of the powder constituents. Preferred appropriate pouring aids of this kind are water-insoluble, hydrophobizing, or moisture-absorbing powders of diatomaceous earth, pyrogenic silicic acids, calcium phosphate, calcium silicates, aluminum oxide, magnesium oxide, magnesium carbonate, zinc oxide, stearates, fatty amines, and the like.

Lastly, preparations (B) can also additionally contain a de-dusting agent that prevents the powdered constituents from forming dust. Inert oils, in particular, can be used for this. The solid cosmetic carriers preferably contain ester oils or mineral oils, and preferably hydrocarbon oils such as liquid paraffin oil, as a de-dusting agent.

The ready-to-use agents are produced, immediately before application to the hair, by mixing the two preparations (A) and (B) or by mixing the three preparations (A) and (B) and (C). In the case of ready-to-use agents that are mixed from more than two preparations to provide a completed mixture for use, it can be irrelevant whether, first, two preparations are mixed with one another, and then the third preparation is added and mixed in, or whether all the preparations are combined together and then mixed. Mixing can be accomplished by stirring in a dish or cup, or by shaking in a closable container.

The two preparations (A) and (B) can be mixed, for example, in a ratio of 1:5 to 5:1, preferably 1:3 to 3:1, and particularly 1:2 to 2:1. If three preparations (A), (B), and (C) are mixed with one another, different mixing ratios are likewise possible, which can range from 1:1:1 to 3:1:1 to 1:3:1 to 1:1:3, for example.

The term, "immediately," is to be understood as a time period from a few seconds to one hour—preferably up to 30 minutes, and in particular up to 15 minutes.

The preparations (A), (B), and, optionally, (C) are used in a method for lightening keratin fibers, and in particular human hair, in which the agent is applied to the keratin-containing fibers, left on the fibers for a contact period from 10 to 60 minutes, and then rinsed out again with water or washed out with a shampoo.

The contact time of the ready-to-use lightening agents is preferably 10 to 60 min, in particular 15 to 50 min, and particularly preferably 20 to 45 min. During the contact time of the agent on the fibers, it may be advantageous to assist the lightening process by low supply of heat. Heat delivery can occur by way of an external heat source e.g., using a warm air blower, and also—in particular, in the case of a hair lightening process on living subjects—by way of the body temperature of the subject. With the latter option, the portion to be lightened is usually covered with a hood. A contact phase at room temperature is preferred. After the contact time has ended, the remaining lightening preparation is rinsed out of the hair with water or with a cleaning agent. A commercially available shampoo can, in particular, serve as a cleaning agent in this context, wherein, in particular, the cleaning agent can then be omitted, and the rinsing-out operation can occur using tap water if the lightening agent possesses a carrier with a high surfactant content.

The above-described preferred embodiments of the agent also apply, mutatis mutandis, to the method.

EXAMPLES

1. Preparation of the Ready-to-Use Lightening Agent by Mixing Two Preparations (A) and (B)

The following preparations were produced (all specifications are in wt % unless indicated otherwise).

| Composition (A) | Wt % |
|---|---|
| Disodium pyrophosphate | 0.1 |
| Dipicolic acid | 0.1 |
| Potassium hydroxide (50% aqueous solution) | 0.3 |
| Cetearyl alcohol | 3.6 |
| Ceteareth-20 | 0.5 |
| Sodium lauryl sulfate | 0.3 |
| PEG-40 castor oil | 0.6 |
| Isopropyl myristate | 10.0 |
| Hydrogen peroxide, 50% aqueous solution | 23.2 |
| Water | up to 100 |

| Preparation (B) | B1 | B2 | B3 | B4 |
|---|---|---|---|---|
| Sodium silicate | 36 | 36 | 36 | 36 |
| Sodium hexametaphosphate | 0.2 | 0.2 | 0.2 | 0.2 |
| Hydroxyethyl cellulose | 0.35 | 0.35 | 0.35 | 0.35 |
| Cekol 50000 (cellulose gum) | 2 | 2 | 2 | 2 |
| Silica | 0.4 | 0.4 | 0.4 | 0.4 |
| Ariabel Blue 300302 CI 77007 (ULTRAMARINES) | 0.15 | 0.15 | 0.15 | 0.15 |
| Potassium persulfate | 32 | 32 | 32 | 32 |
| Ammonium persulfate | 10 | 10 | 10 | 10 |
| Paraffinum Liquidum | 4.5 | 4.5 | 4.5 | 4.5 |
| Dissolvine GL-PD-S N,N-bis(carboxymethyl) glutamic acid tetrasodium salt (GLDA, CAS number 51981-21-6) | 1.6 | 1.6 | 1.6 | 1.6 |
| Lipoid P 20 | — | 3 | — | — |
| Lysine (hydrochloride) | — | — | 3 | — |
| L-valine | — | — | — | 3 |
| Magnesium carbonate | up to 100 | up to 100 | up to 100 | up to 100 |

| Preparation (B) | B5 | B6 | B7 |
|---|---|---|---|
| Sodium silicate | 36 | 36 | 36 |
| Sodium hexametaphosphate | 0.2 | 0.2 | 0.2 |
| Hydroxyethyl cellulose | 0.35 | 0.35 | 0.35 |
| Cekol 50000 (cellulose gum) | 2 | 2 | 2 |
| Silica | 0.4 | 0.4 | 0.4 |
| Ariabel Blue 300302 CI 77007 (ULTRAMARINES) | 0.15 | 0.15 | 0.15 |
| Potassium persulfate | 32 | 32 | 32 |
| Ammonium persulfate | 10 | 10 | 10 |
| Paraffinum Liquidum | 4.5 | 4.5 | 4.5 |
| Dissolvine GL-PD-S N,N-bis(carboxymethyl) glutamic acid tetrasodium salt (CAS number 51981-21-6) | 1.6 | 1.6 | 1.6 |
| L-glutamic acid | 3 | — | — |
| L-arginine | — | 3 | — |
| Glycine | — | — | 3 |
| Magnesium carbonate | up to 100 | up to 100 | up to 100 |

Hair strands (Kerling, Euro natural hair 4-0) were measured colorimetrically (Datacolor Spectraflash SF 450) (L=19.63, a=3.76, b=4.44), pre-shampooed, and dried.

To produce the ready-to-use lightening or bleaching agent, in each case 60 g of preparation (A) were mixed with 60 g of the particular preparation (B). The mixture for use obtained in this way was applied to the strands of hair, left there for 45 minutes, and then rinsed out again with water. The hair strands were then measured again colorimetrically.

The higher the ΔE value, the greater the color shift of the strands compared to the untreated hair. The dE value used for the assessment results from the measured L*a*b* color measurement values as follows:

$$dE=[(L_i-L_0)^2+(a_i-a_0)^2+(b_i-b_0)]^{1/2}$$

$L_0$, $a_0$, and $b_0$=measured values of the strands before the bleaching $L_i$, $a_i$, and $b_i$=measured values of the strands after the bleaching The greater the ΔC value, the greater the difference in the chroma value compared to the untreated hair, wherein the chroma value is calculated as $C=(a^2+b^2)^{1/2}$.

| Mixture for use | L | a | b | ΔE | ΔE |
|---|---|---|---|---|---|
| (A) + (B1), GLDA (comparison) | 55.15 | 8.86 | 29.35 | 43.68 | 25.43 |
| (A) + (B2), GLDA + Lipoid P20 | 54.91 | 9.56 | 30.58 | 44.29 | 26.78 |
| (A) + (B3), GLDA + lysine | 58.53 | 9.63 | 32.18 | 48.14 | 28.35 |
| (A) + (B4), GLDA + valine | 59.14 | 9.37 | 31.33 | 48.12 | 27.47 |
| (A) + (B5), GLDA + glutamic acid | 56.08 | 10.10 | 31.23 | 45.68 | 27.53 |
| (A) + (B6), GLDA + arginine | 60.31 | 9.10 | 32.88 | 49.92 | 28.94 |
| (A) + (B7), GLDA + glycine | 57.22 | 10.01 | 32.54 | 47.35 | 28.79 |

In the case of the hair strands which were bleached using the preparations (B2) through (B7), it was possible to measure particularly high ΔE values and increased ΔC values, i.e., the color shift or color change compared to the starting hair was greatest with these formulations.

2. Preparation of the Ready-to-Use Lightening Agent by Mixing Three Preparations (A), (B), and (C)

The following preparations were produced (all specifications are in wt % unless indicated otherwise).

| Composition (A) | Wt % |
|---|---|
| Disodium pyrophosphate | 0.1 |
| Dipicolic acid | 0.1 |
| Potassium hydroxide (50% aqueous solution) | 0.3 |
| Cetearyl alcohol | 3.6 |
| Ceteareth-20 | 0.5 |
| Sodium lauryl sulfate | 0.3 |
| PEG-40 castor oil | 0.6 |
| Isopropyl myristate | 10.0 |
| Hydrogen peroxide, 50% aqueous solution | 23.2 |
| Water | up to 100 |

| Preparation (B) | Wt % |
|---|---|
| Potassium persulfate | 98.4 |
| Silica (fumed) | 1.6 |

| Preparation © | C1 | C2 | C3 | C4 |
|---|---|---|---|---|
| Cetearyl alcohol | 5.75 | 5.75 | 5.75 | 5.75 |
| Lorol techn. (C12-C18 fatty alcohols) | 2.7 | 2.7 | 2.7 | 2.7 |
| Ceteareth-20 | 0.25 | 0.25 | 0.25 | 0.25 |
| Sodium laureth sulfate (C12-14, 2EO 27% aqueous solution) | 6.0 | 6.0 | 6.0 | 6.0 |
| Ammonium sulfate | 0.5 | 0.5 | 0.5 | 0.5 |
| Ammonia (25% aqueous solution) | 7.6 | 7.6 | 7.6 | 7.6 |

-continued

| | | | | |
|---|---|---|---|---|
| Sodium silicate 40/42 | 0.5 | 0.5 | 0.5 | 0.5 |
| Potassium hydroxide (50% aqueous solution) | 1.0 | 1.0 | 1.0 | 1.0 |
| Dissolvine GL-PD-S N,N-bis(carboxymethyl) glutamic acid tetrasodium salt (CAS number 51981-21-6) | 2.5 | 2.5 | 2.5 | 2.5 |
| Lipoid P20 | — | 0.5 | — | — |
| Lysine (hydrochloride) | — | — | 0.5 | — |
| Valine | — | — | — | 0.5 |
| Water dist. | up to 100 | up to 100 | up to 100 | up to 100 |

| Preparation (C) | C5 | C6 | C7 | C8 |
|---|---|---|---|---|
| Cetearyl alcohol | 5.75 | 5.75 | 5.75 | 5.75 |
| Lorol techn. (C12-C18 fatty alcohols) | 2.7 | 2.7 | 2.7 | 2.7 |
| Ceteareth-20 | 0.25 | 0.25 | 0.25 | 0.25 |
| Sodium laureth sulfate (C12-14, 2EO 27% aqueous solution) | 6.0 | 6.0 | 6.0 | 6.0 |
| Ammonium sulfate | 0.5 | 0.5 | 0.5 | 0.5 |
| Ammonia (25% aqueous solution) | 7.6 | 7.6 | 7.6 | 7.6 |
| Sodium silicate 40/42 | 0.5 | 0.5 | 0.5 | 0.5 |
| Potassium hydroxide (50% aqueous solution) | 1.0 | 1.0 | 1.0 | 1.0 |
| Dissolvine GL-PD-S N,N-bis(carboxymethyl) glutamic acid tetrasodium salt (CAS number 51981-21-6) | 2.5 | 2.5 | 2.5 | 2.5 |
| Serine | 0.5 | — | — | — |
| Glutamic acid | — | 0.5 | — | |
| L-arginine | — | — | 0.5 | — |
| Glycine | — | — | — | 0.5 |
| Water dist. | up to 100 | up to 100 | up to 100 | up to 100 |

Hair strands (Kerling, Euro natural hair 4-0) were measured colorimetrically (Datacolor Spectraflash SF 450) (L=21.15, a=3.85, b=4.39), pre-shampooed, and dried.

To produce the ready-to-use lightening or bleaching agent, in each case 60 g of preparation (A) were mixed with 20 g of preparation (B) and 60 g of preparation (C). The mixture for use obtained in this way was applied to the strands of hair, left there for 45 minutes, and then rinsed out again with water. The hair strands were then measured again colorimetrically.

The higher the ΔE value, the greater the color shift of the strands compared to the untreated hair. The dE value used for the assessment results from the measured L*a*b* color measurement values as follows:

$$dE=[(L_i-L_0)^2+(a_i-a_0)^2+(b_i-b_0)]^{1/2}$$

$L_0$, $a_0$, and $b_0$=measured values of the strands before the bleaching $L_i$, $a_i$, and $b_i$=measured values of the strands after the bleaching The greater the ΔC value, the greater the difference in the chroma value compared to the untreated hair, where the chroma value is calculated as $C=(a^2+b^2)^{1/2}$.

| Mixture for use | L | a | b | ΔE | ΔC |
|---|---|---|---|---|---|
| (A) + (B) + (C1), GLDA (comparison) | 46.6 | 11.09 | 27.27 | 34.98 | 24.00 |
| (A) + (B) + (C2), GLDA + Lipoid P20 | 48.01 | 11.04 | 28.62 | 36.88 | 25.27 |
| (A) + (B) + (C3), GLDA + lysine | 47.24 | 10.83 | 27.62 | 35.62 | 24.26 |
| (A) + (B) + (C4), GLDA + valine | 48.96 | 10.78 | 28.08 | 37.18 | 24.69 |
| (A) + (B) + (C5), GLDA + serine | 46.72 | 10.98 | 27.58 | 35.25 | 24.26 |

-continued

| Mixture for use | L | a | b | ΔE | ΔC |
|---|---|---|---|---|---|
| (A) + (B) + (C6), GLDA + glutamic acid | 47.33 | 11.19 | 28.88 | 36.59 | 25.57 |
| (A) + (B) + (C7), GLDA + arginine | 49.13 | 10.51 | 28.17 | 37.32 | 24.70 |
| (A) + (B) + (C8), GLDA + glycine | 48.8 | 11.55 | 29.68 | 38.25 | 26.44 |

In the case of the hair strands which were bleached using the preparations (C2) through (C8), it was possible to measure particularly high ΔE values and increased ΔC values, i.e., the color shift or color change compared to the starting hair was greatest with these formulations.

3. Lightening Agent, Further Formulation Examples

Preparation of the ready-to-use lightening agent by mixing two preparations (A) and (B).

| Composition (A) | Wt % |
|---|---|
| Disodium pyrophosphate | 0.1 |
| Dipicolic acid | 0.1 |
| Potassium hydroxide (50% aqueous solution) | 0.3 |
| Cetearyl alcohol | 3.6 |
| Ceteareth-20 | 0.5 |
| Sodium lauryl sulfate | 0.3 |
| PEG-40 castor oil | 0.6 |
| Isopropyl myristate | 10.0 |
| Hydrogen peroxide, 50% aqueous solution | 23.2 |
| Water | up to 100 |

| Preparation (B) (wt %) | B1 | B2 | B3 | B4 |
|---|---|---|---|---|
| Sodium silicate | 33.0 | 33.0 | 33.0 | 33.0 |
| Paraffinum Liquidum | 4.5 | 4.5 | 4.5 | 4.5 |
| Sodium hexametaphosphate | 0.2 | 0.2 | 0.2 | 0.2 |
| Degalan RG S mv (methyl methacrylate, methacrylic acid copolymer, Evonik) | 1.0 | 1.0 | 1.0 | 1.0 |
| Polyquaternium-4 | 0.3 | 0.3 | 0.3 | 0.3 |
| Silica (fumed) | 0.4 | 0.4 | 0.4 | 0.4 |
| Potassium persulfate | 32.0 | 32.0 | 32.0 | 32.0 |
| Ammonium persulfate | 10.0 | 10.0 | 10.0 | 10.0 |
| Ariabel Blue 300302 | 0.2 | 0.2 | 0.2 | 0.2 |
| Dimethicones, dimethiconol | 1.5 | 1.5 | 1.5 | 1.5 |
| Dissolvine GL-PD-S N,N-bis(carboxymethyl) glutamic acid tetrasodium salt (CAS number 51981-21-6) | 0.5 | 1.0 | 2.0 | 3.0 |
| L-lysine | 0.9 | — | — | — |
| L-arginine | — | 1.5 | — | — |
| Glycine | — | — | 3.0 | — |
| L-valine | — | — | — | 3.5 |
| Magnesium carbonate | up to 100 | up to 100 | up to 100 | up to 100 |

| Preparation (B) (wt %) | B5 | B6 | B7 | B8 |
|---|---|---|---|---|
| Sodium silicate | 33.0 | 33.0 | 33.0 | 33.0 |
| Paraffinum Liquidum | 4.5 | 4.5 | 4.5 | 4.5 |
| Sodium hexametaphosphate | 0.2 | 0.2 | 0.2 | 0.2 |
| Degalan RG S mv (Methyl methacrylate, methacrylic acid copolymer, Evonik) | 1.0 | 1.0 | 1.0 | 1.0 |
| Polyquaternium-4 | 0.3 | 0.3 | 0.3 | 0.3 |
| Silica (fumed) | 0.4 | 0.4 | 0.4 | 0.4 |
| Potassium persulfate | 32.0 | 32.0 | 32.0 | 32.0 |
| Ammonium persulfate | 10.0 | 10.0 | 10.0 | 10.0 |
| Ariabel Blue 300302 | 0.2 | 0.2 | 0.2 | 0.2 |
| Dimethicones, dimethiconol | 1.5 | 1.5 | 1.5 | 1.5 |
| Dissolvine GL-PD-S N,N-bis(carboxymethyl) glutamic acid tetrasodium salt (CAS number 51981-21-6) | 1.6 | 1.0 | 2.0 | 3.0 |
| Serine | 1.6 | — | — | — |
| L-valine | — | 1.2 | — | — |
| L-glutamic acid | — | — | 3.1 | — |
| Arginine | — | — | — | 3.8 |
| Magnesium carbonate | up to 100 | up to 100 | up to 100 | up to 100 |

By mixing preparation (A) with one of preparations (B1) through (B8) in a ratio of 1:1 in each case, the ready-to-use bleaching agents were produced.

4. Lightening Coloring Agents Produced by Mixing Two Preparations (A) and (B)

| Preparation (A) | Wt % |
|---|---|
| Phosphoric acid 85% | 0.04 |
| Hydrogen peroxide (50% aqueous solution) | 12.00 |
| Emulgade F (INCI: cetearyl alcohol, PEG-40 castor oil, sodium cetearyl sulfate) | 2.10 |
| Sodium benzoate | 0.04 |
| Disodium pyrophosphate | 0.30 |
| Water | up to 100 |

| Preparation (B) | B1 wt % | B2 wt % | B3 wt % | B4 wt % |
|---|---|---|---|---|
| Cetearyl alcohol | 8.00 | 8.00 | 8.00 | 8.00 |
| Paraffinium Liquidum | 7.40 | 7.40 | 7.40 | 7.40 |
| Eumulgin B 3 (INCI: Ceteareth-30) | 1.30 | 1.30 | 1.30 | 1.30 |
| Acrylamidopropyltrimonium chloride/acrylate copolymer | 2.00 | 2.00 | 2.00 | 2.00 |
| P-toluenediamine sulfate | 0.15 | 0.15 | 0.15 | 0.15 |
| Resorcinol | 0.058 | 0.058 | 0.058 | 0.058 |
| m-aminophenol | 0.016 | 0.016 | 0.016 | 0.016 |
| 3-amino-2-methylamino-6-methoxypyridine | 0.005 | 0.005 | 0.005 | 0.005 |
| Potassium hydroxide (50%) | 0.7 | 0.7 | 0.7 | 0.7 |
| Sodium silicate 42 (3,1 $SiO_2$:$Na_2O$) | 0.5 | 0.5 | 0.5 | 0.5 |
| Ammonia (25% aqueous solution) | 5.80 | 5.80 | 5.80 | 5.80 |
| Perfume | 0.40 | 0.40 | 0.40 | 0.40 |
| Dissolvine GL-PD-S N,N-bis(carboxymethyl) glutamic acid tetrasodium salt (CAS number 51981-21-6) | 0.4 | 0.6 | 0.8 | 1.5 |
| L-arginine | 1.0 | 0.3 | — | — |
| Lysine HCI | — | 0.3 | 2.0 | 0.5 |
| L-valine | — | 0.6 | — | 2.5 |
| Glycine | — | — | — | — |
| Water | up to 100 | up to 100 | up to 100 | up to 100 |

Preparation (A) was in each case mixed with preparation (B) in a ratio of 1:1.

The invention claimed is:

1. An agent for oxidatively changing the color of keratin fibers, the agent comprising:

at least one complexing agent of general formula (I),

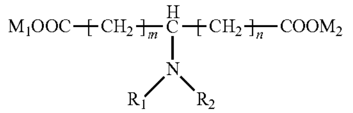

(I)

wherein:

R1 and R2, independently of one another, represent a carboxy-$C_1$-$C_6$ alkyl group or a physiologically acceptable salt thereof, a hydrogen atom, a $C_1$-$C_6$ alkyl group, or a hydroxy-$C_2$-$C_6$ alkyl group, m represents an integer from 0 to 6, n represents an integer from 0 to 6, and M1 and M2, independently of one another, represent a hydrogen atom or an equivalent of an alkali metal ion, an alkaline earth metal ion, a metal ion, or an ammonium ion ($NH_4^+$); and at least one activator that is a phosphoglyceride; and at least one oxidant.

2. The agent of claim 1, wherein R1 and R2, independently of one another, represent a carboxy-$C_1$-$C_6$ alkyl group or a physiologically acceptable salt thereof.

3. The agent of claim 1, wherein:

m represents the number 0 or 1, and/or n represents the number 0, 1, or 2.

4. The agent of claim 1, wherein the at least one complexing agent has the general formula (Ia), (Ia)

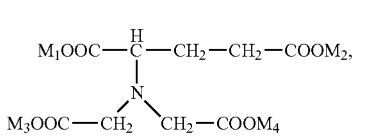

wherein:

M1 and M2, independently of one another, represent a hydrogen atom or an equivalent of an alkali metal ion, an alkaline earth metal ion, or a metal ion; and M3 and M4, independently of one another, represent a hydrogen atom or an equivalent of an alkali metal ion, an alkaline earth metal ion, a metal ion, or an ammonium ion ($NH_4^+$).

5. The agent of claim 1, wherein the at least one or more complexing agent is present, based on the total weight of the agent, in an amount ranging from 0.01 to 10.0 wt %.

6. The agent of claim 1, wherein the at least one activator is present, based on the total weight of the agent, in an amount ranging from 0.01 to 10.0 wt %.

7. The agent of claim 1, wherein a weight ratio of the at least one complexing to the at least one activator is from 0.1 to 10.

8. The agent of claim 1, wherein the at least one oxidant is selected from the group consisting of hydrogen peroxide, ammonium peroxodisulfate, potassium peroxodisulfate, sodium peroxodisulfate, and any combination thereof.

9. The agent of claim 1, further comprising water, wherein the agent has a pH value ranging from 7.5 to 11.5.

10. A method for oxidatively changing the color of keratin fibers, the method comprising:

applying the agent of claim 1 to the keratin fibers; and rinsing out the agent from the keratin fibers following a contact time.

11. The agent of claim 1, wherein the keratin fibers are human hair.

12. The agent of claim 1, wherein the metal ion is selected from the group consisting of sodium, potassium, ½ magnesium, ½ calcium, and ½ zinc.

13. The agent of claim 3, wherein m represents the number 0 and n represents the number 2.

14. The agent of claim 1, wherein the at least one activator has the general formula (II),

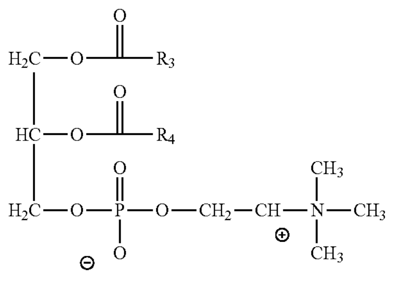

(II)

wherein:

R3 and R4, independently of one another, represent a saturated or unsaturated $C_{11}$-$C_{29}$ alkyl group, and at least one of R3 or R4 represents an unsaturated C11-C29 alkyl group.

15. The agent of claim 14, wherein at least one of the group R3 or the group R4 represents an at least monounsaturated $C_{15}$-$C_{21}$ alkyl group.

* * * * *